United States Patent
Inaba et al.

(10) Patent No.: US 9,557,326 B2
(45) Date of Patent: Jan. 31, 2017

(54) SAMPLE ANALYZING DEVICE AND SAMPLE ANALYZING METHOD

(75) Inventors: Toru Inaba, Tokyo (JP); Shinya Matsuoka, Hitachinaka (JP); Taku Sakazume, Hitachinaka (JP); Yoshihiro Yamashita, Hitachinaka (JP); Masafumi Shimada, Hitachinaka (JP); Osamu Kogi, Yokohama (JP); Yushi Harada, Ushiku (JP)

(73) Assignee: Hitachi High-Technologies Corporation, Tokyo (JP)

( * ) Notice: Subject to any disclaimer, the term of this patent is extended or adjusted under 35 U.S.C. 154(b) by 173 days.

(21) Appl. No.: 13/702,175

(22) PCT Filed: Jun. 7, 2011

(86) PCT No.: PCT/JP2011/063046
§ 371 (c)(1),
(2), (4) Date: Feb. 19, 2013

(87) PCT Pub. No.: WO2011/155489
PCT Pub. Date: Dec. 15, 2011

(65) Prior Publication Data
US 2013/0143234 A1    Jun. 6, 2013

(30) Foreign Application Priority Data

Jun. 9, 2010 (JP) .................................. 2010-131579
Mar. 30, 2011 (JP) .................................. 2011-073876
Jun. 2, 2011 (JP) .................................. 2011-123910

(51) Int. Cl.
*G01N 33/543* (2006.01)
*G01N 33/53* (2006.01)
(Continued)

(52) U.S. Cl.
CPC ............. *G01N 33/5306* (2013.01); *B03C 1/01* (2013.01); *B03C 1/033* (2013.01); *B03C 1/0332* (2013.01);
(Continued)

(58) Field of Classification Search
CPC  G01N 27/3275; G01N 27/3278; G01N 15/10; G01N 15/1031; G01N 33/54326; B82Y 35/00; B82Y 25/00; B01L 2400/043
See application file for complete search history.

(56) References Cited

U.S. PATENT DOCUMENTS 5,123,901 A  6/1992  Carew
5,744,367 A  4/1998  Talley et al.
(Continued)

FOREIGN PATENT DOCUMENTS

JP  07-209189 A  8/1995
JP  07-248330 A  9/1995
(Continued)

OTHER PUBLICATIONS

English translation of International Preliminary Report on Patentability from International Patent Application No. PCT/JP2011/063046, dated Jan. 15, 2013.

*Primary Examiner* — Rebecca Martinez
(74) *Attorney, Agent, or Firm* — Miles & Stockbridge P.C.

(57) ABSTRACT

This invention provides a sample analyzing device and sample analyzing method designed to suppress nonuniform capture of magnetic particles (10) and detect a desired substance with higher accuracy. The sample analyzing device includes a flow channel (15) that conducts thereinto a sample which contains the magnetic particles (10), and magnetic field generating means (12) that generates magnetic fields for capturing the magnetic particles (10) in a (Continued)

magnetic particles capturing region of the flow channel (15); wherein the flow channel has at least one of structural characteristics that a cross-sectional area of the flow channel, at a downstream end of the magnetic particles capturing region, is larger than a cross-sectional area of the flow channel, at an upstream end of the magnetic particles capturing region, and that the magnetic fields generated by the magnetic field generating means (12) have a greater magnitude at a downstream side of the magnetic particles capturing region than at an upstream side thereof.

20 Claims, 13 Drawing Sheets

(51) Int. Cl.
  *B03C 1/033* (2006.01)
  *B03C 1/28* (2006.01)
  *B03C 1/01* (2006.01)
  *G01N 33/574* (2006.01)
  *G01N 35/00* (2006.01)

(52) U.S. Cl.
  CPC ......... *B03C 1/288* (2013.01); *G01N 33/54326* (2013.01); *G01N 33/57438* (2013.01); *G01N 33/57484* (2013.01); *B03C 2201/18* (2013.01); *B03C 2201/22* (2013.01); *B03C 2201/24* (2013.01); *B03C 2201/26* (2013.01); *G01N 35/0098* (2013.01)

(56) References Cited

U.S. PATENT DOCUMENTS

| | | | | |
|---|---|---|---|---|
| 5,993,740 | A | * 11/1999 | Niiyama | G01N 33/54326 209/215 |
| 2006/0020371 | A1 | * 1/2006 | Ham et al. | 700/266 |
| 2006/0081954 | A1 | * 4/2006 | Tondra et al. | 257/421 |
| 2009/0053799 | A1 | * 2/2009 | Chang-Yen et al. | 435/287.2 |
| 2010/0123457 | A1 | 5/2010 | Shinoda | |

FOREIGN PATENT DOCUMENTS

| | | |
|---|---|---|
| JP | 08-062224 A | 3/1996 |
| JP | 09-210999 A | 8/1997 |
| JP | 10-509798 A | 9/1998 |
| JP | 11-242033 A | 9/1999 |
| JP | 2000-065833 A | 3/2000 |
| JP | 2008-051813 A | 3/2008 |
| WO | WO 02/26292 A1 | 4/2002 |
| WO | WO2006/136996 | * 12/2006 |
| WO | WO2007/021814 | * 2/2007 |

* cited by examiner

SAMPLE ANALYZING DEVICE AND SAMPLE ANALYZING METHOD

TECHNICAL FIELD

The present invention relates generally to devices and methods for analyzing samples, and more particularly to a sample analyzing device and sample analyzing method utilizing reactions between an antigen and an antibody.

BACKGROUND ART

First, immunoassay is described below as an example of sample analysis.

Immunological testing uses specific reactions between an antigen and an antibody, to detect or quantitatively measure the antibody or antigen in a body fluid such as plasma, serum, or urine, and diagnose a disease, a pathological state, and the like. Enzyme-linked immunosorbent assay (ELISA) is available as a typical method of immunological testing. In the ELISA method, an antibody against an antigen which is to be assayed is immobilized as a first antibody in a bottom portion of a container and then a sample of plasma, serum, or urine is added in the container to bind the antigen in the sample to the first antibody. In addition, an antibody with a label bound thereto is further bound as a second antibody to the antigen bounded to the first antibody, and then a signal emitted from the label can be detected. The presence and quantity of antigen in the sample is thus assayed. A fluorescent substance, for example, is used as the label. In this case, intensity of the light emitted from the fluorescent substance increases in proportion to the number of second antibodies having the label bounded thereto, that is, the quantity of antigen, and using a photomultiplier or the like to detect the light emitted from the fluorescent substance will allow quantification of the antigen in the sample.

In a more specific example of an immunological test device using an ELISA method, magnetic particles are used as a solid phase, with a first antibody being immobilized to the surface of the magnetic particles. A substance with a fluorescent dye bounded thereto as a label, that is, a fluorochrome-labeled substance is bound to a second antibody. When an antigen-antibody reaction is caused by mixing a biologically derived detection substance (antigen) and the magnetic particles having the first antibody immobilized thereto, a specific antigen contained in the sample binds to the magnetic particles via the first antibody. When the second antibody is further made to react, the fluorochrome-labeled substance binds to the magnetic particles via the second antibody, the antigen, and the first antibody. The quantity of fluorochrome-labeled substance depends upon, and thus increases or decreases with, the quantity of detection substance contained in the sample, that is, upon the quantity of antigen.

After the magnetic particles with the detection substance bounded thereto have been captured onto a specific region, a laser or the like is activated for that solution. The fluorochrome-labeled substance bound to the magnetic particles will then emit light. Detection of the intensity of the emitted light will allow the quantity of detection substance in the sample, that is, the quantity of antigen, to be assayed. That is to say, the antigen in the sample can be quantitatively measured.

To conduct highly sensitive immunoassay, the magnetic particles with the detection substance (antigen) bounded thereto are captured onto a specific region using a magnet or the like, and while the magnetic particles remain captured, the solution that contains antibodies unbound to the antigen of interest is replaced with a new solution. That is to say, bound antigen-antibody aggregates and free (unbound) ones are separated from each other. This operation is called "bound/free (B/F) separation".

Methods for causing magnetic particles to be captured onto a capturing region in an analyzing device are described in Patent Documents 1 and 2.

PRIOR ART LITERATURE

Patent Documents

Patent Document 1: JP-1996-62224-A
Patent Document 2: JP-1999-242033-A

SUMMARY OF THE INVENTION

Problems to be Solved by the Invention

However, capturing the magnetic particles onto the capturing region poses the following problems.

When the magnetic particles are captured onto the magnetic particles capturing region, a distribution of the capturing often becomes nonuniform. As a result, during the solution replacement for B/F separation, surface tension of the solution has allowed the solution to remain at aggregative magnetic particles, thus rendering sufficient B/F separation unachievable.

In addition, when magnetic particles are gathered at a specific region for detection, a capturing distribution of the magnetic particles usually becomes nonuniform. As a result, accumulation of the magnetic particles has occasionally decreased light emission sensitivity and hence, measuring performance.

The present invention has been made with the above in mind, and an object of the invention is to provide a sample analyzing device and sample analyzing method designed to suppress nonuniform adsorption of magnetic particles onto a capturing region and detect an antibody or antigen with higher accuracy.

Means for Solving the Problems

In accordance with an aspect of the present invention, there is provided a sample analyzing device including a flow channel that conducts thereinto a sample which contains magnetic particles, and magnetic field generating means that generates magnetic fields for capturing the magnetic particles in a magnetic particles capturing region of the flow channel. The flow channel has at least one of structural characteristics that a cross-sectional area of the flow channel, at a downstream side of the magnetic particles capturing region, is larger than a cross-sectional area of the flow channel, at an upstream side of the magnetic particles capturing region, and that the magnetic fields generated by the magnetic field generating means have a greater magnitude at a downstream side of the magnetic particles capturing region than at an upstream side thereof.

In accordance with another aspect of the present invention, there is provided a sample analyzing device including a flow channel that conducts thereinto a sample which contains magnetic particles, magnetic field generating means that generates, in the flow channel, magnetic fields for capturing the magnetic particles in a capturing region of the flow channel, and analyzing means that analyzes the captured magnetic particles. The sample analyzing device is configured so that the magnetic fields generated by the magnetic field generating means have a greater magnitude at a downstream side of the flow channel, on the capturing region, than at an upstream side of the flow channel.

In accordance with yet another aspect of the present invention, there is provided a sample analyzing method including conducting a sample containing magnetic particles into a flow channel, activating magnetic field generating means to generate magnetic fields in a magnetic particles capturing region of the flow channel, and capturing the magnetic particles. In the sample analyzing method, the sample is conducted into the magnetic particles capturing region constructed to have a larger flow-channel cross-sectional area at a downstream side thereof than a flow-channel cross-sectional area at an upstream side thereof, and/or to ensure that the magnetic fields generated by the magnetic field generating means have a greater magnitude at a downstream side of the magnetic particles capturing region than at an upstream side thereof. In addition, the magnetic field generating means generates the magnetic fields and captures the magnetic particles.

Effects of the Invention

By using the above means, nonuniform adsorption can be suppressed so that improved B/F separation and cleaning efficiency, enhanced measurement accuracy, and higher measurement variation are anticipated.

MODES FOR CARRYING OUT THE INVENTION

Hereunder, examples of implementing the present invention will be described using the accompanying drawings.

First Example

Immunoassay devices will be described as examples of a sample analyzing device which is an embodiment of the present invention. The present invention can be applied not only to immunoassays, but also to any sample analyzing device that uses magnetic particles and captures the magnetic particles by switching magnetic field strength. That is to say, the invention provides a technique similarly useable for other analyzing devices as well, for example, analyzers associated with DNA, biochemistry, and the like.

Figure 9:
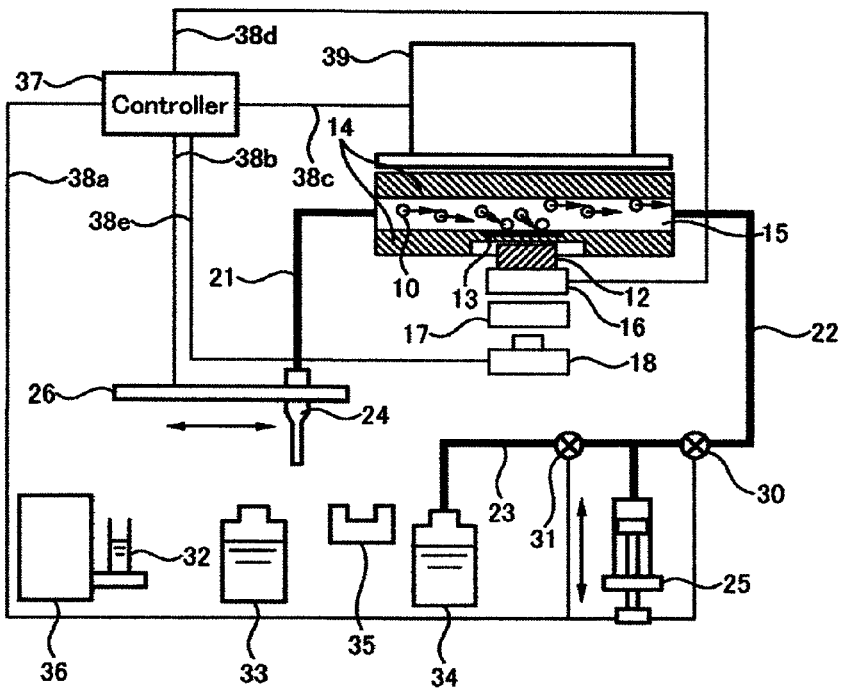
FIG. 9 shows an example of a sample analyzing device.

A schematic configuration diagram of an immunoassay device as a first example, is shown in FIG. 9. Referring to FIG. 9, a flow channel 15 is connected to a sipper nozzle 24 and a pump 25 through tubes 21 and 22. The sipper nozzle 24 is mounted to be movable by an arm 26, and a suspension container 32 and a rinsing container 33 are placed within a moving range of the sipper nozzle 24.

A valve 30 is connected to the tube 22, between the flow channel 15 and the pump 25. The pump 25, controlled from a controller 37 through a signal line 38a, can aspirate and discharge a preset amount of liquid accurately. The tube 22 is further routed to a waste liquid container 34 through a tube 23.

Flow channel walls 14 of a detection unit (flow cell) are formed from a transparent material, and the flow channel through which a solution flows is formed internally to the flow channel walls 14. Since the flow channel walls 14 are entirely formed from the transparent material, the walls transmit light and are constructed to allow a flow state of the solution inside the walls to be observed. The flow channel walls 14 may not be entirely formed from the transparent material. Instead, only the section of the flow channel walls 14 that transmits light may be formed from the transparent material as a window.

The transparent flow channel walls of the detection unit are preferably manufactured using a material that is substantially transparent or translucent with respect to a wavelength of the light emitted from a labeled substance of magnetic particles complex which has been adsorbed in the adsorbing portion of the flow cell. A preferable material is, for example, glass, quartz, plastic, or the like.

A laser light source 18 and a condensing lens 17 are set up around a lower section of the flow channel 15. Laser light from the laser light source 18 is condensed by the condensing lens 17 and then reaches a capturing position 13 within the flow channel 15.

Additionally, the immunoassay device uses a magnet 12 (11) as magnetic field application means to cause the capturing of magnetic particles. When the device causes the capturing of the magnetic particles, the device moves the magnet 12 directly below the flow channel 15. For example, the magnet 12 (11) is mounted on a sliding mechanism 16 that is free to move in a horizontal direction, and when the magnetic particles are to be captured, the device moves the magnet 12 (11) directly below the flow channel 15. For cleaning an internal section of the flow channel 15, the device moves the magnet 12 (11) to a position in which an influence of the magnet can be sufficiently reduced, and the movement enables sufficient cleaning. While the sliding mechanism 16 is used to move the magnet 11 in the horizontal direction, the magnet 12 (11) may be moved in a vertical direction if an influence of the magnetic fields due to the movement of the magnet 12 (11) is sufficiently reduced for cleaning.

The capturing position 13 in the flow channel 15 needs to be irradiated with the laser light condensed by the condensing lens 17 after the laser light source 18 has emitted the light from the lower periphery of the flow channel 15. The region that serves as the capturing position 13 in the flow channel walls 14 of the detection unit, therefore, is preferably manufactured using a material that is substantially transparent or translucent with respect to the wavelength of the light emitted from the labeled substance of the magnetic particles complex which has been captured in the capturing portion of the flow cell. For example, the substantially transparent or translucent material is preferably glass, quartz, plastic, or the like. Alternatively, for example if the laser light source 18 and the condensing lens 17 are arranged or configured to make it unnecessary for the light to pass through the capturing position 13, the region to serve as the capturing position 13 is preferably manufactured from gold, platinum, carbon-containing, or any other equivalent material, allowing for bringing the magnet 12 (11) close to the underside of that region and capturing the magnetic particles complex on the upside.

The controller 37 is connected to a photodetector 39 and a pump 31, as well as to the arm 26, the sliding mechanism 16, the laser light source 18, the pump 25, and the pump 30, and can control these elements.

Inside the flow channel 15, the magnetic particles 10 are captured in a planarly spread condition onto the capturing region 13 by a magnetic force of the magnet 12 (11). The magnetic force of the magnet 12 (11) is released when the emitted light is measured. During the release, however, since the flow of the liquid inside the flow channel 15 is already stopped, the magnetic particles 10 remain in a captured condition inside the flow channel 15. After the application of the magnetic fields to the flow channel 15 has been released, laser light irradiation from the laser light source 18 placed below the flow channel 15 causes fluorescent light to be emitted with the magnetic particles 10 remaining captured to the capturing region 13. The light emitted from the labeled substance on the magnetic particles 10 is then detected, whereby light from a solid phase is measured with high sensitivity.

The flow channel 15 is formed from a light-transmissive material, so the channel is constructed of one material selected from candidates, such as acryl, that have a high light transmittance. The photodetector 39 can be, for example, a CCD camera or a photomultiplier.

A sample to be analyzed is that derived from a biological fluid such as serum or urine. If the sample is serum, the kind of specific component to be analyzed is, for example, a variety of tumor markers, antibodies, antigen-antibody complexes, or single proteins. The first example assumes that the specific component is TSH (Thyroid-Stimulating Hormone).

After being mixed with a beads solution and a reagent during a pretreatment process to react therewith for a fixed time at a constant temperature of 37° C.), the sample to be analyzed is accommodated in the suspension container 32.

The beads solution is a solution prepared by dispersing in a buffer the magnetic particles 10 which were created by embedding magnetic particulate matter in a matrix such as polystyrene, and streptavidin bindable to biodin is bound onto a surface of the matrix.

The reagent includes a substance that binds the magnetic particles 10 to TSH, the specific component in the sample, and an anti-TSH antibody with biotin-treated terminals is included in the binding substance.

The reagent differs according to the kind of specific component to be analyzed. For example, an immunoglobulin, an antigen, an antibody, or any other appropriate biological substance is used as the reagent.

The rinsing container 33 contains a rinsing used to clean internal surface of the flow channel 15 and the tube 21.

The flow channel 15 is desirably formed to have a width greater than a depth (i.e., thickness or height) by a factor of two to twenty. This makes it easy for the particles introduced into the flow of the fluid along with it, to spread in a lateral direction of the flow. It is desirable that the magnetic particles should ideally spread in single-layer form, but in fact, overlapping between the particles more or less occurs.

An capturing distribution of the particles in the flow channel 15 is determined by a balance between the magnetic force based on the magnetic field from the magnet 12 (11) under the flow channel 15 and a drag due to the liquid flow during introduction of the suspension containing the reaction mixture. The magnetic fields in the flow channel 15 preferably range between about 0.1 and 0.5 T inclusive. A preferable flow velocity of the liquid in that case ranges between about 0.05 and 0.10 m/s inclusive. Where the force depending on the flow velocity exceeds a force with which the magnet captures the particles by the magnetic force, the particles are released, for which reason, the appropriate flow velocity needs to be selected.

The magnetic particles 10 are used as the solid phase, having a particle size of 1 to 10 μm and a specific gravity of 1.3 to 1.5. The magnetic particles 10 refuse to sink into the liquid and are easy to suspend therein. The magnetic particles 10 have an immobilized antibody on a surface of each.

The magnetic particles are preferably at least one of the following particles:
(1) Particles that exhibit paramagnetism, superparamagnetism, ferromagnetism, or ferrimagnetism
(2) Particles that contain the particles that exhibit paramagnetism, superparamagnetism, ferromagnetism, or ferrimagnetism, in a material such as a synthetic high polymer (polystyrene, nylon, or the like), native compound (cellulose, agarose, or the like), inorganic compound (silica, glass, or the like)

Particle sizes of these magnetic particles range preferably between 0.01 μm and 200 μm, and further preferably between 1 μm and 10 μm. Their specific gravity preferably ranges between 1.3 and 1.5. A substance having a nature to specifically bind the substance to be analyzed, for example an antibody having a nature to specifically bind to an antigen, binds onto the surface of each magnetic particle.

The labeled substance is preferably at least one of the following specifically bound to the target molecule by use of appropriate means and made luminescent by use of appropriate means:
(1) A labeled substance used in a fluorescent immunoassay method. For example, an antibody labeled with fluorescein isothiocyanate.
(2) A labeled substance used in a chemiluminescent immunoassay method. For example, an antibody labeled with acridinium ester.
(3) A labeled substance used in a chemiluminescent enzyme immunoassay method. For example, an antibody labeled with a chemiluminescent enzyme whose luminescent substrate is luminol or an adamantyl derivative.

Next, operation of the present embodiment is described below.

One analytical cycle includes a suspension aspirating period, a particles capturing period, a detection period, a cleaning period, a resetting period, and a preliminary aspiration period. One cycle starts upon completion of positioning of the suspension container 32 containing the suspension previously treated in a reaction unit 36.

In the suspension aspirating period, a signal from the controller 37 activates the sliding mechanism 16 to move the magnet 12 (11) downward to the lower section of the flow channel 15. This opens the valve 30 and closes the valve 31. Another signal from the controller 37 operates the arm 26 to insert the sipper nozzle 24 into the suspension container 32. After this, yet another signal from the controller 37 activates the pump 25 to start a fixed amount of aspiration. Next, the suspension in the suspension container 32 is aspirated into the tube 21 through the sipper nozzle 24 by an action of a liquid inside the tube 21. After the fixed amount of aspiration, the controller 37 stops the pump 25 and then operates the arm 26 to insert the sipper nozzle 24 into a cleaning mechanism 35. While passing through the cleaning mechanism 35, the sipper nozzle 24 is cleaned at its front end.

In the particle capturing period, the pump 25 aspirates the suspension at a fixed rate in accordance with a signal from the controller 37. The suspension existing in the tube 21 during this period flows through the flow channel 15. Since the magnetic fields from the magnet 12 (11) are occurring inside the flow channel walls 14, the magnetic particles 10 contained in the suspension are aspirated towards the magnet 12 (11) and captured onto a capturing position 13.

In the detection period, the sliding mechanism 16 operates to move the magnet 12 (11) away from the flow channel 15. Following this, lasing from the laser light source in accordance with a signal from the controller 37 is started to irradiate the capturing position 13 with the laser light through the condensing lens 17. At this time, light is emitted from a fluorochrome bound to each magnetic particle 10 in the capturing position 13. The fluorescent light is wavelength-selected through a filter and then detected by the photodetector 39 such as a CCD camera or photomultiplexer. Intensity of the emitted light is detected by the photodetector 39 and sent as a signal to the controller 37. Lasing is stopped after a fixed time has passed. During the detection period, the controller 37 operates the arm 26 to insert the sipper nozzle 24 into the cleaning mechanism 35.

In the cleaning period, the rinsing that has been aspirated from the rinsing container 33 using the pump 25 flows through the flow channel 15. Since the magnet 12 (11) is already distanced away at this time, the magnetic particles 10 flow away with the buffer, instead of becoming retained on the capturing position.

In the resetting period, the valve 30 is closed and the valve 31 is opened to start the discharge operation of the pump 25. The liquid in the pump 25 is then discharged into the waste liquid container 34.

In the preliminary aspiration period, the buffer is aspirated, filling the inside of the tube 21 and the flow channel 15. Next cycle becomes executable after the preliminary aspiration period.

Figure 10:
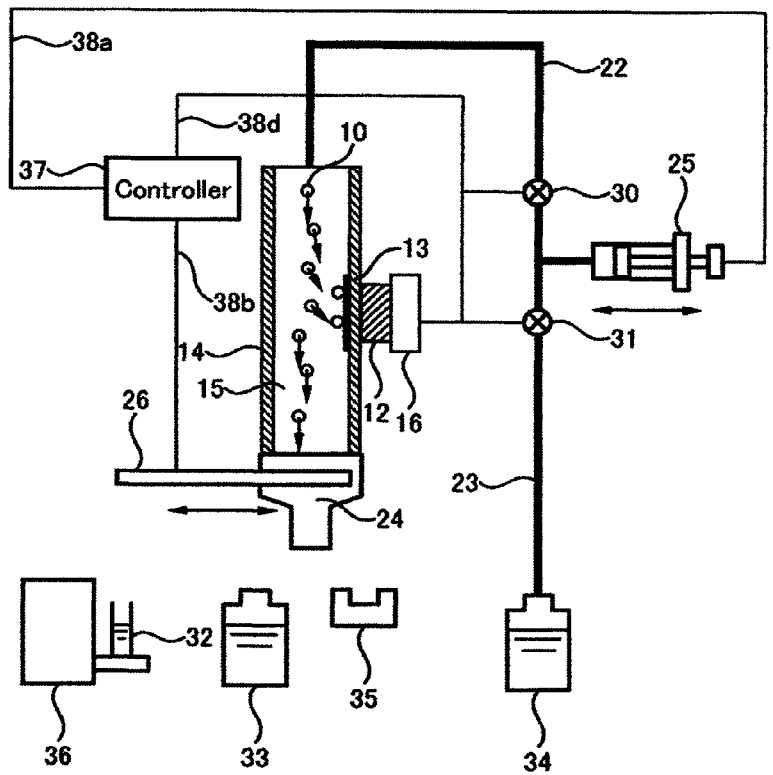
FIG. 10 shows another example of a sample analyzing device.

FIG. 10 shows another example of a sample analyzing device according to the present embodiment, this figure assuming that a capturing position is present inside a sipper nozzle 24 to implement efficient B/F separation. The figure shows the same orientation between the sipper nozzle 24 and flow channel walls 14 having the capturing position 13. Magnetic particles are captured onto the capturing position 13 and then a pump 25 is activated to discharge an unnecessary solution and aspirate a new solution, whereby B/F separation is conducted. As with the device of FIG. 9, B/F separation efficiency is improved by causing uniform capturing distribution of the magnetic particles 10 onto the capturing position 13.

Figure 1:
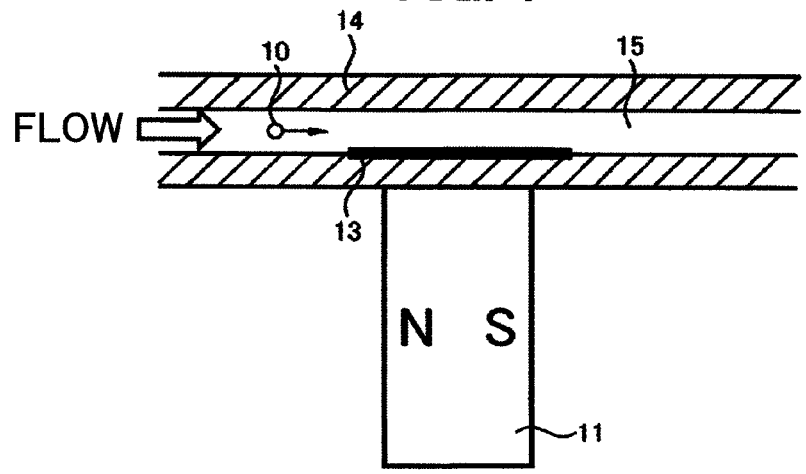
FIG. 1 shows magnetic field generating means in which magnetic fields of a magnet are parallel to a flow direction.

A relationship in position between a flow channel 15 and magnet 11 in a conventional device is shown in FIG. 1.

In FIG. 1 showing the relationship in position between the flow channel 15 and the magnet 11, a magnetic field gradient of the magnet 11 increases at an end portion thereof, which results in a large number of particles becoming captured at an upstream side of a capturing region. If a distance between the flow channel 15 and the magnet 11 is extended for a smaller magnetic field gradient, a decrease in a force exerted upon the magnetic particles 10 will lead to a larger number of particles flowing away without being captured onto a capturing position 13. This will significantly reduce measuring sensitivity.

Figure 3:
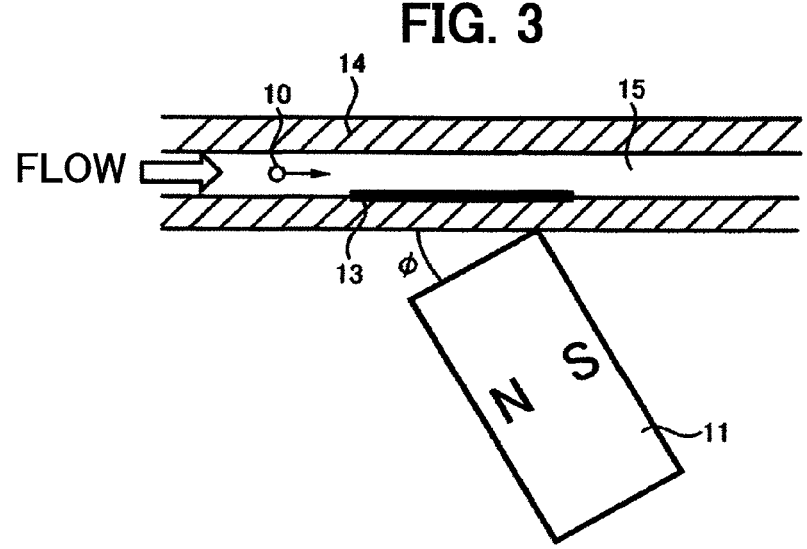
FIG. 3 shows magnetic field generating means in which a magnet is inclined with respect to a flow direction.

FIG. 3 shows a relationship in position between a flow channel 15 and magnet 11 in an embodiment of the present invention.

In a case of FIG. 3, since the magnet 11 is positioned with an inclination with respect to the flow channel 15, a distance between an upstream side of the magnet 11 and the flow channel 15 increases, which prevents an excessively large number of magnetic particles 10 from becoming captured. At a downstream side of the magnet 11, particles become captured in large quantities since a distance between the magnet 11 and the flow channel 15 decreases in comparison with the distance at the upstream side. Consequently, as in FIG. 1 showing the relationship in position between the flow channel 15 and magnet 11 in the conventional device, the magnetic particles can be captured uniformly in the capturing position 13 without becoming captured in excessively large quantities at the upstream side.

The shape and disposition of the magnet in the conventional device increases the gradient of the magnetic fields at the end portion of the magnet placed near the capturing position, thus increases the force exerted from the magnet upon the magnetic particles, and hence increases the number of particles captured at the upstream side. This has deteriorated uniformity of the particle capturing in the capturing position.

In contrast, if the magnet is placed so that its upstream end having a large magnetic field gradient is distanced away from the flow channel with respect to the flow direction of the solution inside the channel, the force exerted from the magnet upon the magnetic particles will not be excessively large, which will in turn prevent an excessively large number of magnetic particles from being captured at the upstream side. This will result in nonuniformity being suppressed.

Figure 2:
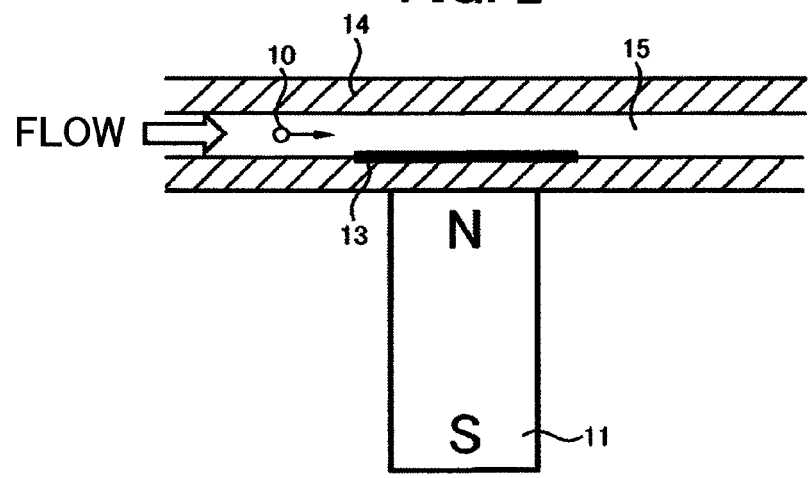
FIG. 2 shows magnetic field generating means in which magnetic fields of a magnet are perpendicular to a flow direction.
Figure 4:
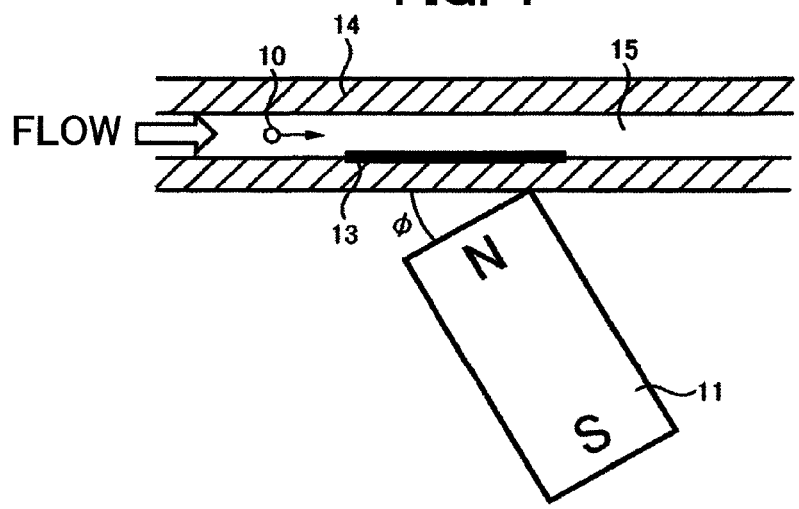
FIG. 4 shows magnetic field generating means in which a magnet is inclined with respect to a flow direction.

FIGS. 1 and 3 show a case in which the direction of flow inside the flow channel 15 and that of magnetic poles of the magnet 11 are substantially the same. FIGS. 2 and 4, on the other hand, show a case in which the direction of flow inside the flow channel 15 and that of the magnetic poles of the magnet 11 are nearly 90 degrees shifted from each other. In the case that the direction of flow inside the flow channel 15 and that of the magnetic poles of the magnet 11 are nearly 90 degrees shifted, inclining the magnet for a greater distance at an upstream side of the capturing position, as in FIG. 4, not FIG. 2, will bring about substantially the same advantageous effects as obtained in the case that the direction of flow inside the flow channel 15 and that of the magnetic poles of the magnet 11 are the same. Analytical results based on calculated behavior of the magnetic particles 10 indicate that an appropriate angle of the inclination is less than 10 degrees with respect to the flow direction. Greater angles lessen the force acting on the magnetic particles 10.

Figure 5:
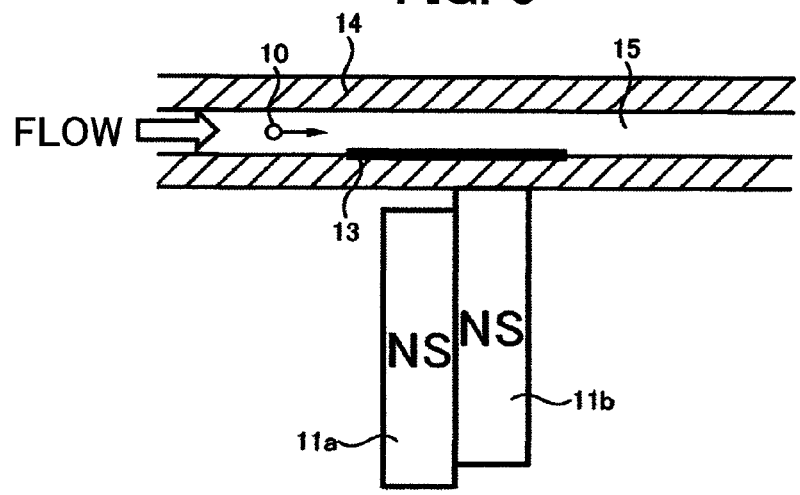
FIG. 5 shows an example of magnetic field generating means constructed of a plurality of magnets, the magnets each being different in distance with respect to a capturing region.
Figure 6:
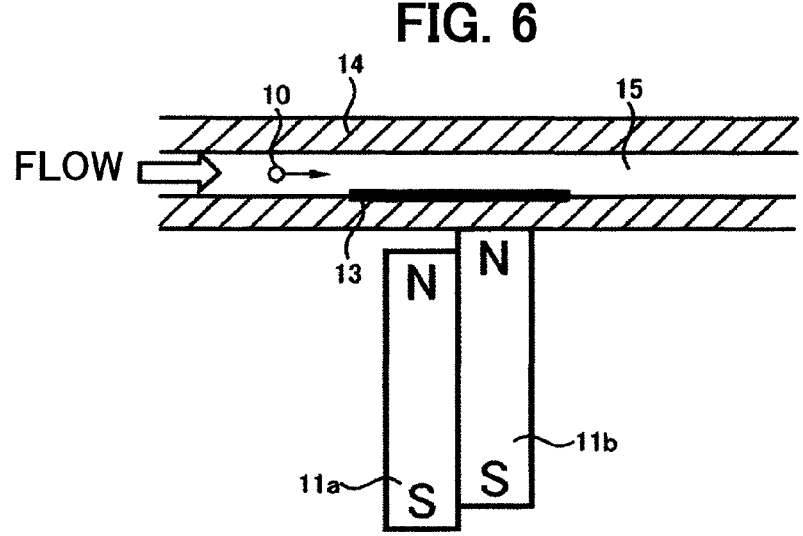
FIG. 6 shows another example of magnetic field generating means constructed of a plurality of magnets, the magnets each being different in distance with respect to a capturing region.

FIGS. 5 and 6 show other examples relating to magnetic field generating means (a magnetic field generator) for achieving uniform capture of magnetic particles 10 in the capturing position 13. A plurality of magnets, 11a and 11b, are used as the magnetic field generating means (the magnetic field generator). These magnets, however, differ from each other in terms of the distance to the capturing position 13 in the flow channel 15. At the upstream side of the flow channel 15, the distance between the channel 15 and the magnet 11a is long, and at the downstream side of the flow channel 15, the distance between the channel 15 and the magnet 11b is short. This layout enables uniform capture in the capturing position 13, without quantitatively excessive capture at the upstream side.

Figure 7:
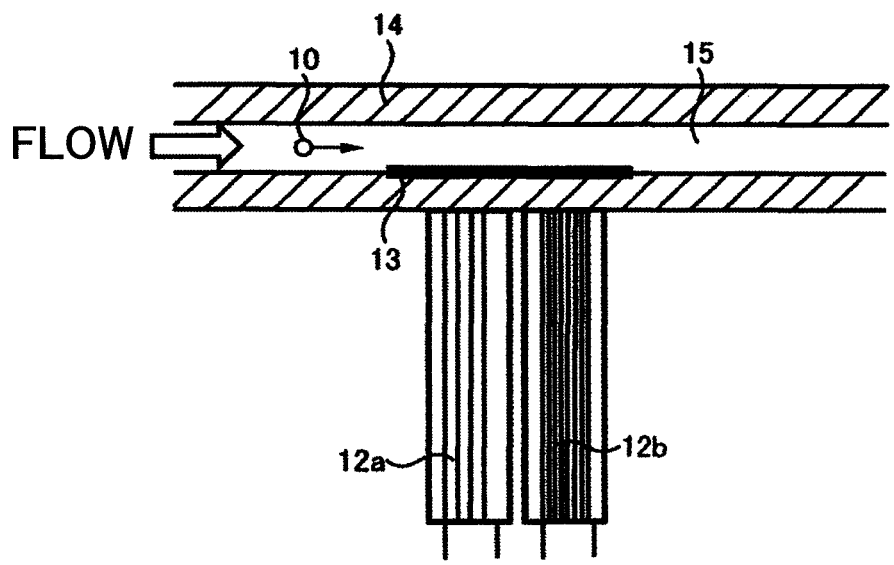
FIG. 7 shows an example of magnetic field generating means constructed of a plurality of electromagnets.
Figure 8:
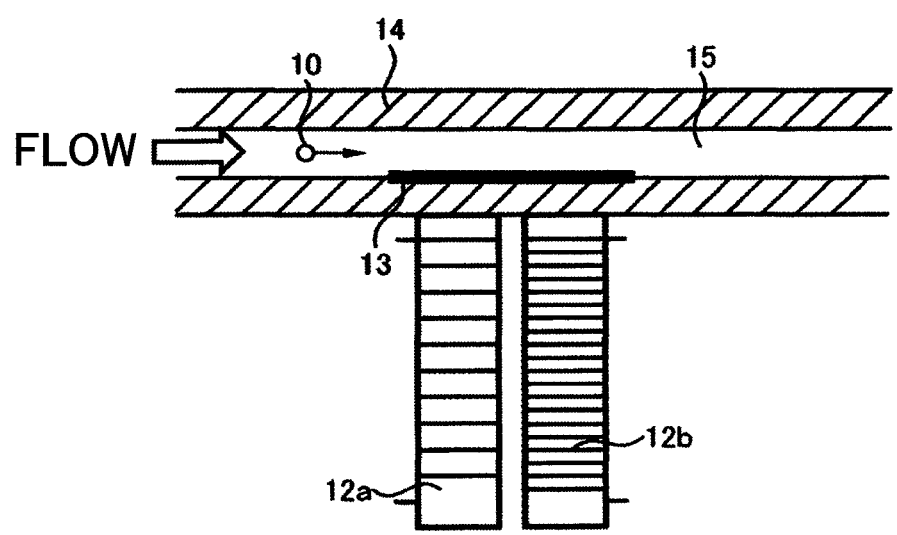
FIG. 8 shows another example of magnetic field generating means constructed of a plurality of electromagnets.

FIGS. 7 and 8 show further examples relating to magnetic field generating means for achieving the uniform capture of magnetic particles in the capturing position 13. A plurality of electromagnets 12 are used as the magnetic field generating means. The electromagnets 12a and 12b, however, differ from each other in terms of the number of windings and in electric current value. More specifically, the number of windings and the current value are small at the upstream side of the flow channel 15 and large at the downstream side thereof. This provides substantially the same advantageous effects as those of FIGS. 5 and 6, lessens the force acting on the magnetic particles 10 at the upstream side, and augments the force acting on the magnetic particles 10 at the downstream side. Uniform capture in the capturing position 13 without quantitatively excessive capture at the upstream side is consequently achieved.

Figure 11:
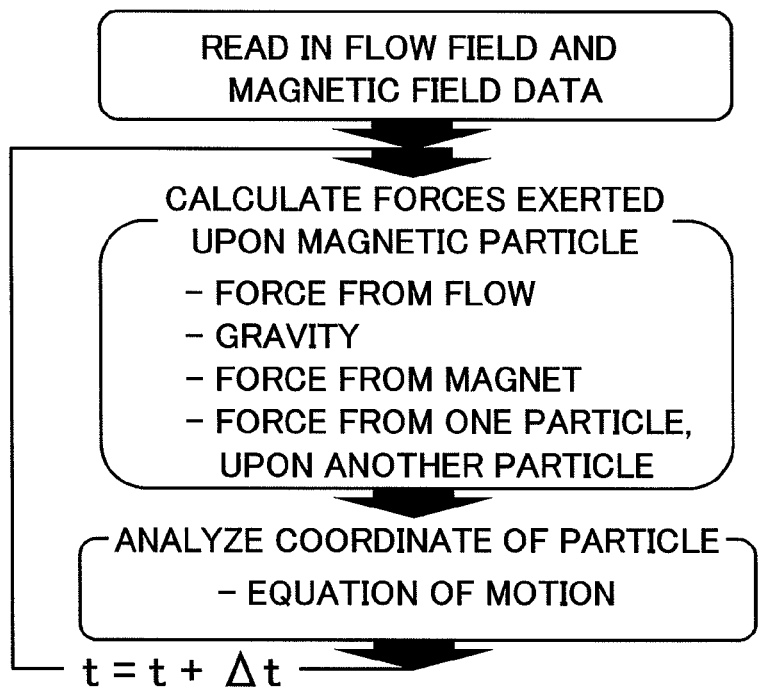
FIG. 11 is a flowchart of magnetic particles movement analysis.

In order to verify the effects of the present invention, behavior analyses were performed using a digital simulator capable of analyzing a movement of magnetic particles. FIG. 11 shows a flowchart of the magnetic particles movement analyses in flow fields, magnetic fields, and gravitational fields. The fluid in the detection flow channel is analyzed using general-purpose computational fluid dynamics software to calculate velocity fields and pressure fields. At the same time, the magnetic fields around the magnet are calculated using general-purpose magnetic-field analysis software. Next, a particles movement program reads in data relating to the flow fields and the magnetic fields. This enables forces upon the particles to be calculated using the data relating to the flow field and magnetic field at each particle position. A force to which the particles are subjected by flow, gravity, a force to which the particles are subjected by the magnet, and a force that one particle exerts upon another particle are assessed as the forces imposed upon the particles. While updating the positions of the particles, the present inventors analyzed the behavior of the particles by sequentially solving the Newton's equation of motion for each particle.

Figure 12A:
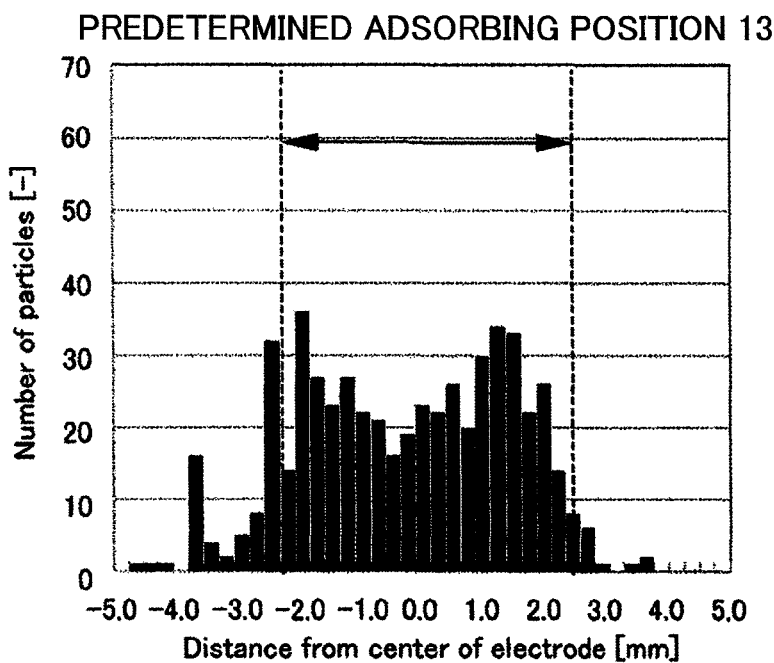
FIG. 12A shows an example of an advantageous effect of the present invention, based on magnetic particles movement analysis.
Figure 12B:
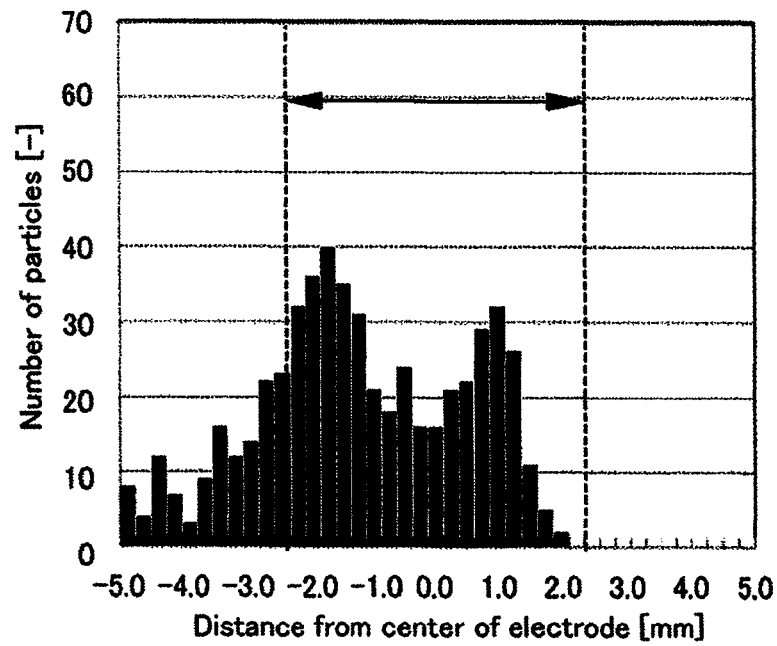
FIG. 12B shows another example of an advantageous effect of the present invention, based on magnetic particles movement analysis.

FIG. 12A shows a particle density distribution of the captured magnetic particles 10 in the flow direction of the fluid in the magnetic field generator as used under the positional relationship between the flow channel 15 and the magnet 11, shown in FIG. 3. The angle that the magnetic poles with respect to the flow direction is 5 degrees. For comparison purposes, analytical results that were obtained using the magnetic field generating means (FIG. 1) of the conventional device are shown in FIG. 12B. The use of the conventional magnetic field generating means causes a large number of particles to be captured at the upstream side of the capturing position 13 and results in nonuniform capture in the capturing position. In contrast to this, the use of the magnetic field generating means having the magnet 11 inclined with respect to the flow direction of the flow channel 15 in the present invention leads to uniform capture as a result of improvement of the situation under which the large number of particles have been initially captured at the upstream side of the capturing region.

Second Example

Another example of the present embodiment, that is, a second example of a sample analyzing device, employs a magnet different from that of the first example. Except for the magnet, the flow cell and all other elements of the sample analyzing device are substantially the same as in the first example, so the same reference number is only assigned to each of the same elements and detailed description thereof is omitted hereinafter.

Figure 13:
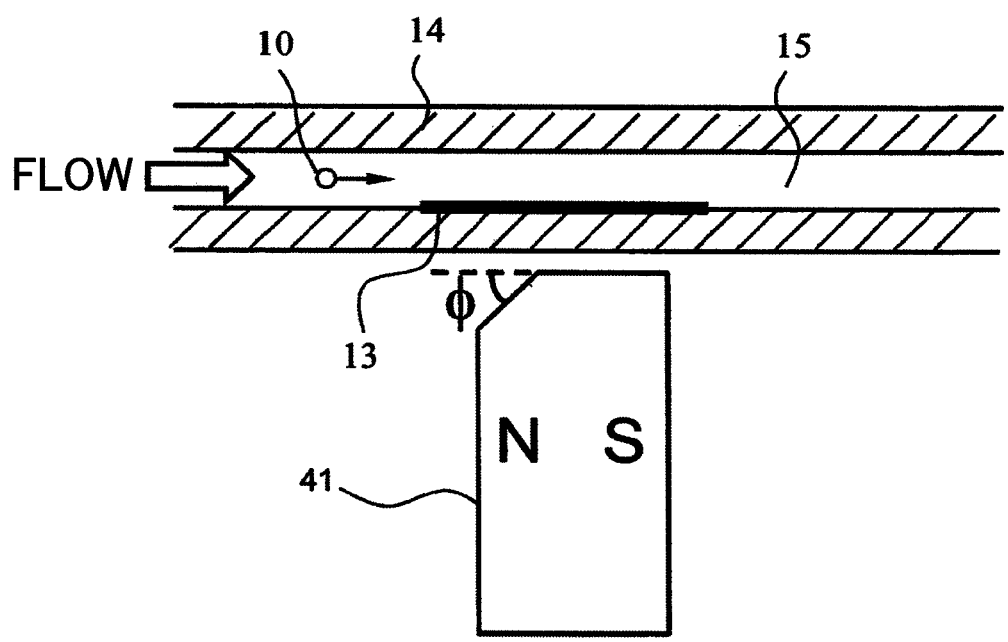
FIG. 13 is a diagram that shows shapes and relative positions of a flow cell and magnet in a sample analyzing device.
Figure 15:
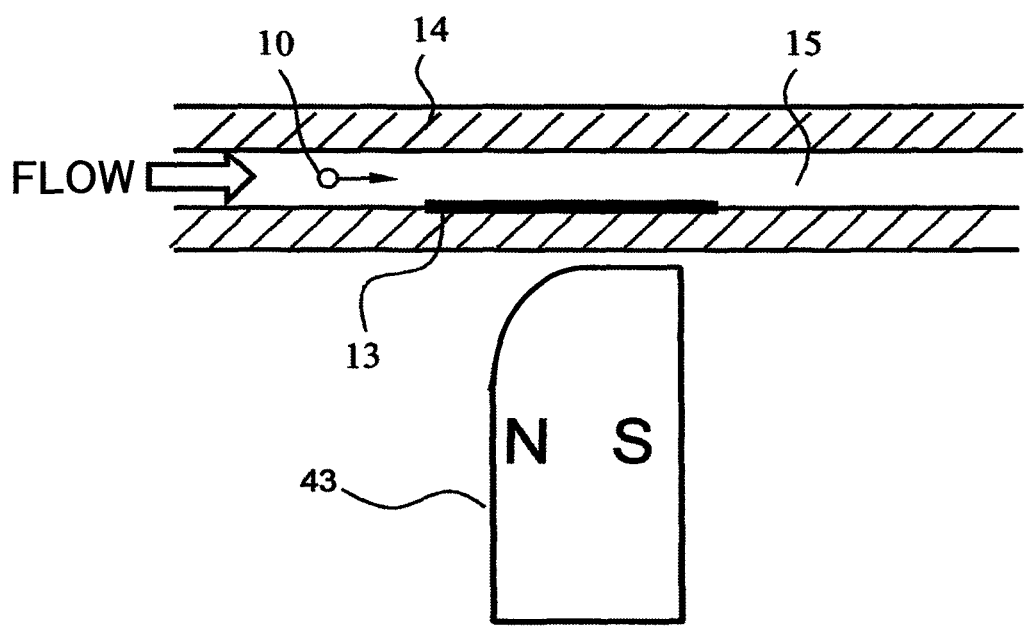
FIG. 15 is a diagram that shows shapes and relative positions of a flow cell and magnet in yet another sample analyzing device.

FIGS. 13 and 15 shows shapes and relative positions of the flow cells and magnets 41, 43 in the sample analyzing device configurations disclosed in the present invention. Referring to FIGS. 13 and 15, the shapes of the magnets 41, 43 are asymmetrical between the upstream side and downstream side of the flow cell. In both figures, the distance between the capturing position 13 of the flow cell and the upstream side of the magnet 41, 43 is long and the distance between the capturing position 13 of the flow cell and the downstream side of the magnet 41, 43 is short. The magnetic particles 10 in the flow of the sample liquid (suspension) through the upstream side of the capturing region which is the flow channel 15 over the capturing position 13 have a great concentration, but the small magnetic fields prevent the magnetic particles from being captured in excessively large quantities. At the downstream side of the capturing region, on the other hand, the magnetic particles in the sample liquid have already been captured at the upstream side and have therefore decreased in numbers, such that even if the flow cell and the magnet are brought closer to each other for stronger magnetic fields and the magnetic particles are captured in this state, the quantity of magnetic particles captured will not be excessive. As a result, nonuniform adsorption of the magnetic particles 10 will not occur, but they will be uniformly captured at high density and in single-layer form in the capturing region.

Figure 14:
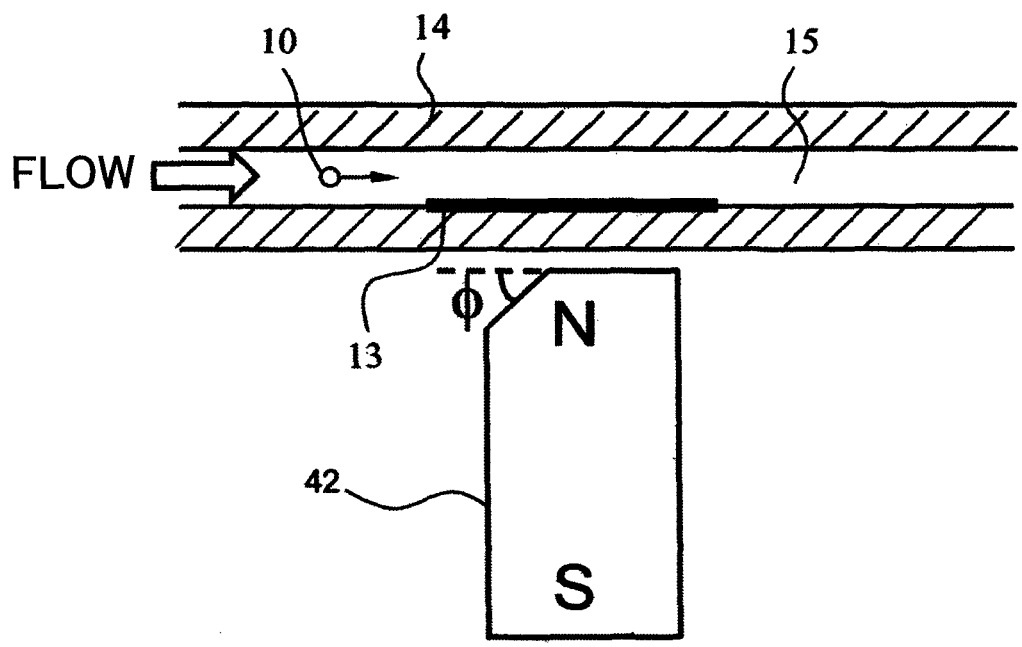
FIG. 14 is a diagram that shows shapes and relative positions of a flow cell and magnet in another sample analyzing device.
Figure 16:
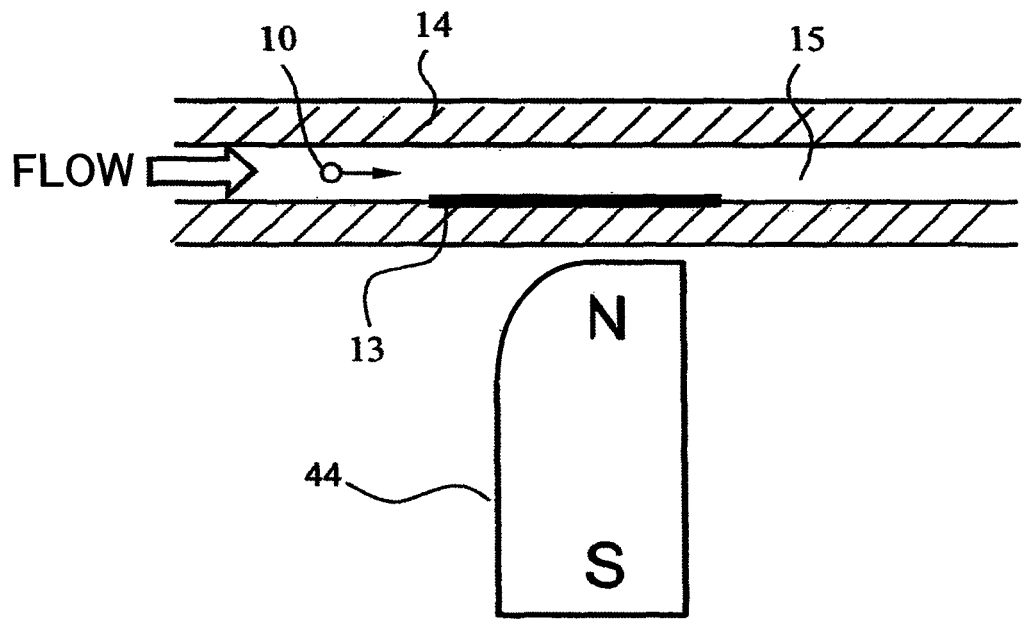
FIG. 16 is a diagram that shows shapes and relative positions of a flow cell and magnet in a further sample analyzing device.

FIGS. 13 and 15 shown a case in which the direction of the magnetic poles of the magnet 41, 43 is substantially parallel to the flow direction of the sample liquid in the flow cell and a wall surface of the capturing position 13. FIGS. 14 and 16 show a case in which, as opposed to this, a direction of magnetic poles of a magnet 42, 44 is substantially perpendicular to the flow direction of the sample liquid in the flow cell and the wall surface of the capturing position 13. In both cases, the asymmetrical shape of the magnet between the upstream side and downstream side of the flow cell yields substantially the same advantageous effects.

In the present example, the magnets 41 to 44 each have a shape with a somewhat sharply or circularly cut upper left corner of a regular parallelepiped, this corner being closer to the flow channel and to the upstream side of the flow of the sample liquid, and with a lower surface substantially parallel to the wall surface of the capturing position 13. This means that since a portion of the conventional magnet shown in FIG. 1, for example, is only cut off, parts for mounting the magnet of the conventional sample analyzer can be used as it is and thus the conventional sample analyzer is easy to change in shape.

In addition, the magnet 41 to 44 is substantially parallel at a downstream side of its upper surface to the flow cell. At the downstream side, the magnet is of a shape allowing it to be brought closer to the flow cell to strengthen the magnetic fields as far as possible within a performance range of the magnet. The cutoff section of the magnet, at the upstream side thereof, preferably has a size that creates an inclination angle ranging between 15 and 45 degrees with respect to a direction parallel to the flow cell. This angle range is desirable for preventing local adherence of the magnetic particles, since the strength of the magnetic fields in the flow cell progressively increases between the upstream side and the downstream side. If, as shown in FIGS. 15 and 16, there is a change in the inclination angle, a desirable average angle of inclination of the inclined section is 15 to 45 degrees. For an ordinary magnet size, inclinations smaller than 15 degrees are too ineffective, causing local adsorption because of an abrupt increase in magnetic field strength at an upstream end of the magnet. Inclinations greater than 45 degrees also result in local adsorption since the magnetic field strength abruptly increases at where the upper surface of the magnet bends.

Furthermore, while being basically a regular parallelepiped in shape, the magnet can have a similar shape created by removing a portion of any other shape such as a column, cylinder, or prism. Since the mounting parts for the conventional magnet are to be used, a magnetization direction of the magnet, as with the conventional magnet, is desirably made either substantially parallel to the flow channel 15 by arranging the N-pole and the S-pole in a horizontal direction, or substantially perpendicular to the flow channel 15 by arranging the N-pole and the S-pole in a vertical direction. While the present example has assumed a permanent magnet as the magnet, this magnet can be an electromagnet instead. In this case, the magnet will have an iron core located close to the flow channel and formed into a shape cut off at a corner near an upstream side of the magnet. The shape cut off at the corner near the upstream side of the magnet is not only a shape created by later removing a portion of the magnet's basic structural member, but also includes a shape recessed from the beginning.

Effects of the sample analyzing device and sample analyzing method disclosed in the present invention are described in detail below. The present example uses magnetic particles of 2.8 µm in average particle size. Width of the predetermined adsorbing position 13 in the flow direction of the solution, in the flow cell, is 5 mm. Width of the magnet in the flow direction of the solution is 3 mm. Coordinates with an origin at the upstream end of the predetermined adsorbing position 13 are taken and the magnet is disposed from the underside of the flow cell, in a 2-to-5 mm (3 mm) coordinate range from the predetermined adsorbing position 13.

Figure 17:
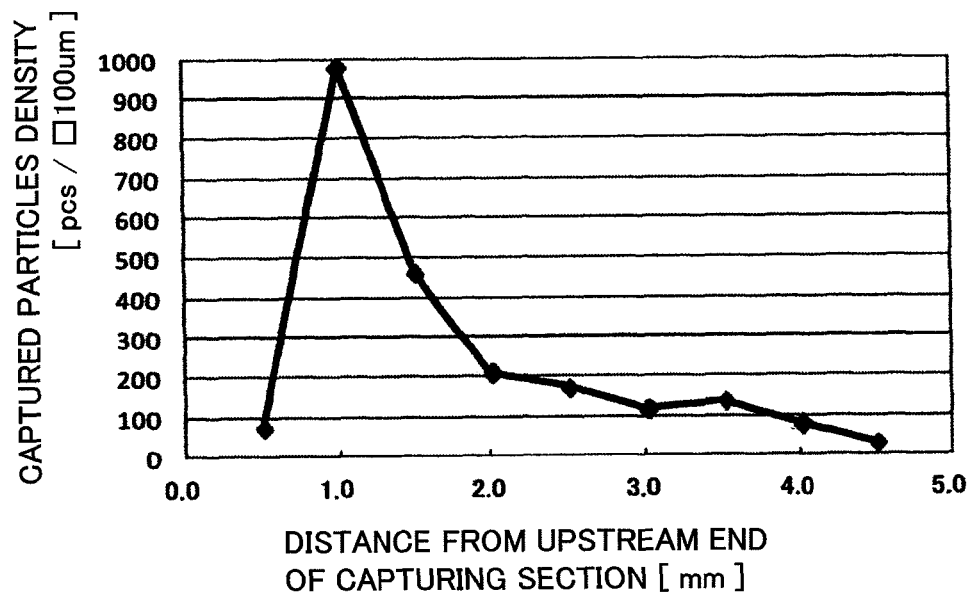
FIG. 17 is a diagram that represents a relationship between a position on a capturing region in a flow cell and a capturing density of magnetic particles at the particular region.

FIG. 17 is a diagram that represents a relationship between a position on the capturing portion 13 in the flow cell and an capture density of magnetic particles at the particular position, the shapes and relative positions of the flow cell and the magnet in this figure being those employed in the conventional device shown in FIG. 1. The diagram indicates that a significant increase in particle capture density at the upstream side of the capturing position 13 leads to accumulation of particles. The result is that in the capturing region as a whole, the particle capture density becomes nonuniform.

Figure 18:
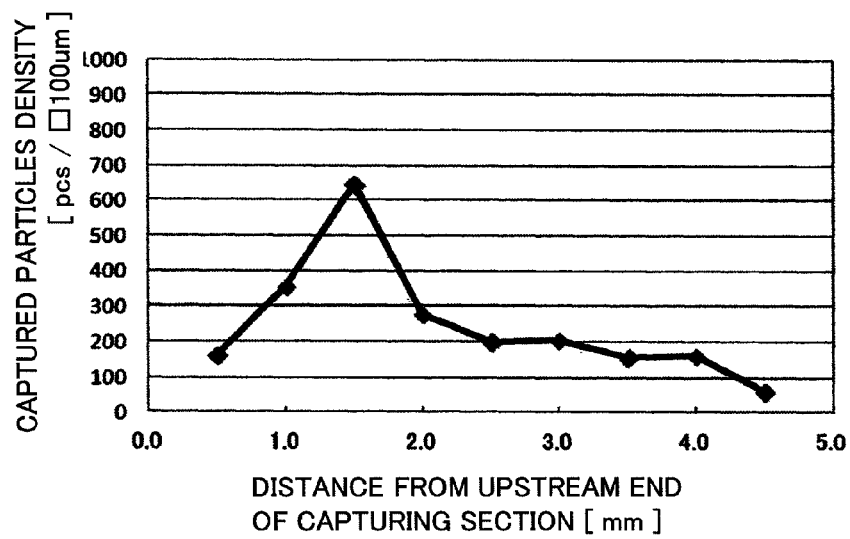
FIG. 18 is another diagram that represents a relationship between a position on a capturing region in a flow cell and a capturing density of magnetic particles at the particular region.

FIG. 18 is a diagram that represents a relationship between a position on the capturing region 13 in the flow cell and an capture density of magnetic particles at the particular position, the shapes and relative positions of the flow cell and the magnet in this figure being those employed in the device shown in FIG. 13. The magnet has an inclination angle of 45 degrees at the upstream side, taking a shape asymmetrical between the upstream side and the downstream side. The diagram indicates that the particle capture density, compared with that of FIG. 17, decreases at the upstream side of the capturing position 13, and that the magnetic particles do not accumulate. The result is that a uniform particle capture density is obtained in the capturing region as a whole.

Third Example

Yet another example of the present embodiment, that is, a third example of a sample analyzing device, employs a flow channel different from that of the first example. Except for the flow channel, the magnet and all other elements of the sample analyzing device are substantially the same as in the first example, so the same reference number is only assigned to each of the same elements and detailed description thereof is omitted hereinafter.

Figure 19A:
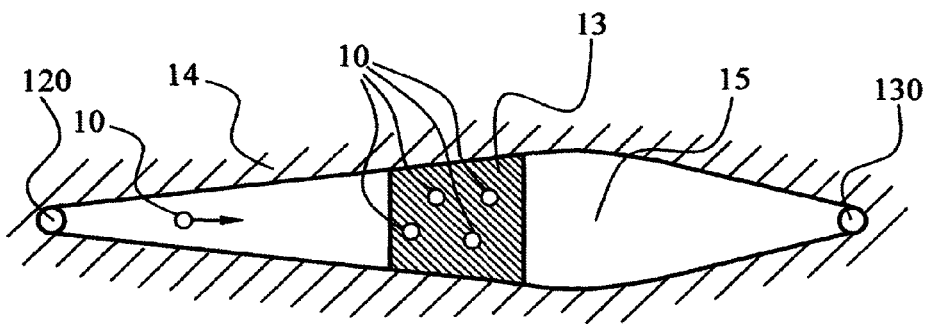
FIG. 19A is a plan sectional view of a flow channel and periphery in a detection unit of an embodiment.
Figure 19B:
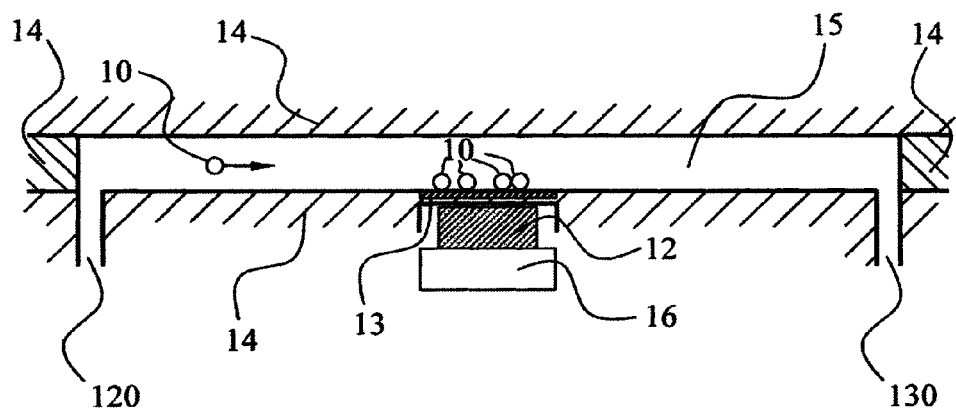
FIG. 19B is a side sectional view of the flow channel and periphery in the detection unit of the embodiment.

FIGS. 19A and 19B show a configuration of the flow channel 15 and periphery in the detection unit of the sample analyzing device shown as the third example of the present embodiment in FIG. 9. FIG. 19A is a plan sectional view of the flow channel 15 and periphery in the detection unit of the present example. FIG. 19B is a side sectional view of the flow channel 15 and periphery in the detection unit of the present example. As shown in FIG. 19A, the flow channel 15 in the present example is constructed so that the width of the channel, at least on and above the capturing position 13, increases in a monotonous and linear pattern with respect to the flow direction of the fluid. In addition, as shown in FIG. 19B, the flow channel 15 is constructed so that height of the channel, at least on and above the capturing position 13, is constant. The magnet 12 has a shape symmetrical between the upstream side and downstream side of the detection unit, and a distance between the capturing position 13 in the detection unit and the magnet 12 is constant. The magnet 12 is constructed so that its longitudinal dimension, that is, a dimension in a direction parallel to the flow direction, is smaller than a dimension of the capturing position 13 that is parallel to the flow direction. The magnet 12 is also constructed to have an upstream end positioned downstream of an upstream end of the capturing position 13, and a downstream end positioned upstream of a downstream end of the capturing position 13.

As shown in FIGS. 19A and 19B, the flow channel 15 and the periphery thereof are constructed so that the suspension containing the magnetic particles 10, supplied from a flow channel inlet 120 provided in a left end of a lower wall of the flow channel walls 14, passes through the capturing position 13 and its periphery, provided in a central region of the flow channel 15, and is discharged from a flow channel outlet 130 provided in a right end of the lower wall of the flow channel walls 14. As shown in FIG. 19A, the flow channel 15 is further constructed so that the width of the channel, from the channel inlet 120 to a position further downstream with respect to the downstream end of the capturing position 13, increases in a monotonous and linear pattern with respect to the flow direction of the fluid, and so that the width of the channel, from the position further downstream with respect to the downstream end of the capturing position 13 to the flow channel outlet 130, decreases in a monotonous and linear pattern with respect to the flow direction of the fluid. In addition, as shown in FIG. 19B, the flow channel 15 is constructed so that the height of the channel, from the channel inlet 120 to the channel outlet 130, is constant.

Figure 20A:
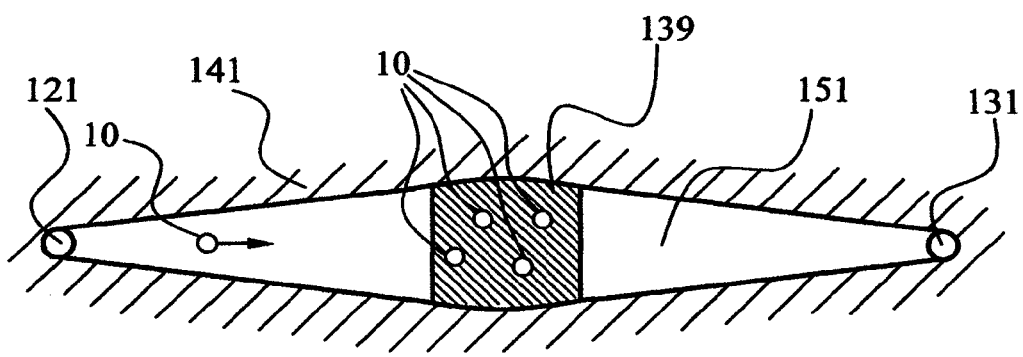
FIG. 20A is a plan sectional view of a flow channel and periphery in a comparative example of a detection unit.
Figure 20B:
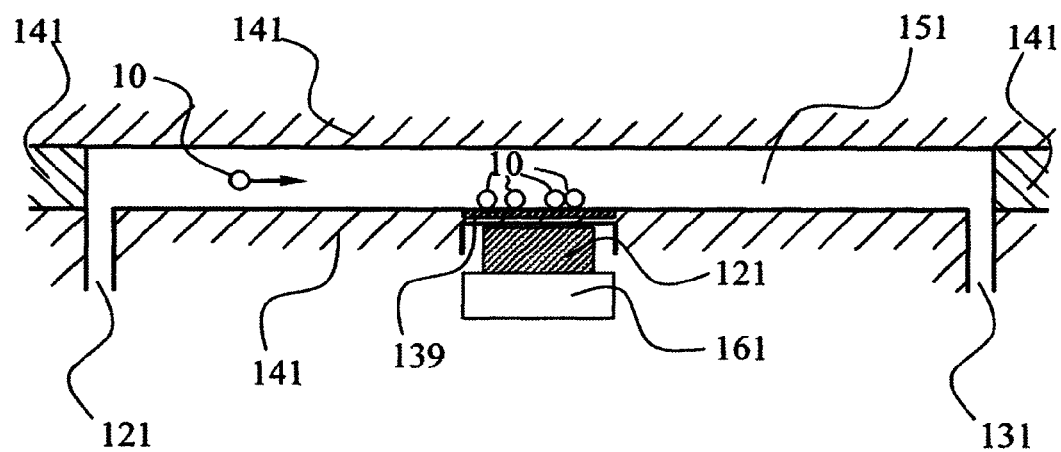
FIG. 20B is a side sectional view of the detection unit flow channel and periphery in the comparative example.

FIGS. 20A and 20B show a configuration of a flow channel 151 and periphery in a detection unit shown as a comparative example. FIG. 20A is a plan sectional view of the flow channel 151 and periphery in the detection unit shown as the comparative example. FIG. 20B is a side sectional view of the flow channel 151 and periphery in the detection unit as the comparative example. As shown in FIGS. 20A and 20B, the flow channel 151 in the comparative example differs from the flow channel 15 in the detection unit of the present example shown in FIGS. 19A and 19B, primarily in that the width of the flow channel at the capturing position 13 is substantially constant.

As shown in FIGS. 20A and 20B, the flow channel 151 and periphery in the comparative example are constructed so that a suspension containing magnetic particles 10, supplied from a flow channel inlet 121 provided in a left end of a lower wall of flow channel walls 141, passes through a capturing position 139 and its periphery, provided in a central portion of the flow channel 151, and is discharged from a flow channel outlet 131 provided in a right end of the lower wall of the flow channel walls 141.

Next, impacts that the flow channel width at the capturing position 139 causes to the flow of the fluid in the flow channel are described below.

Figure 21:
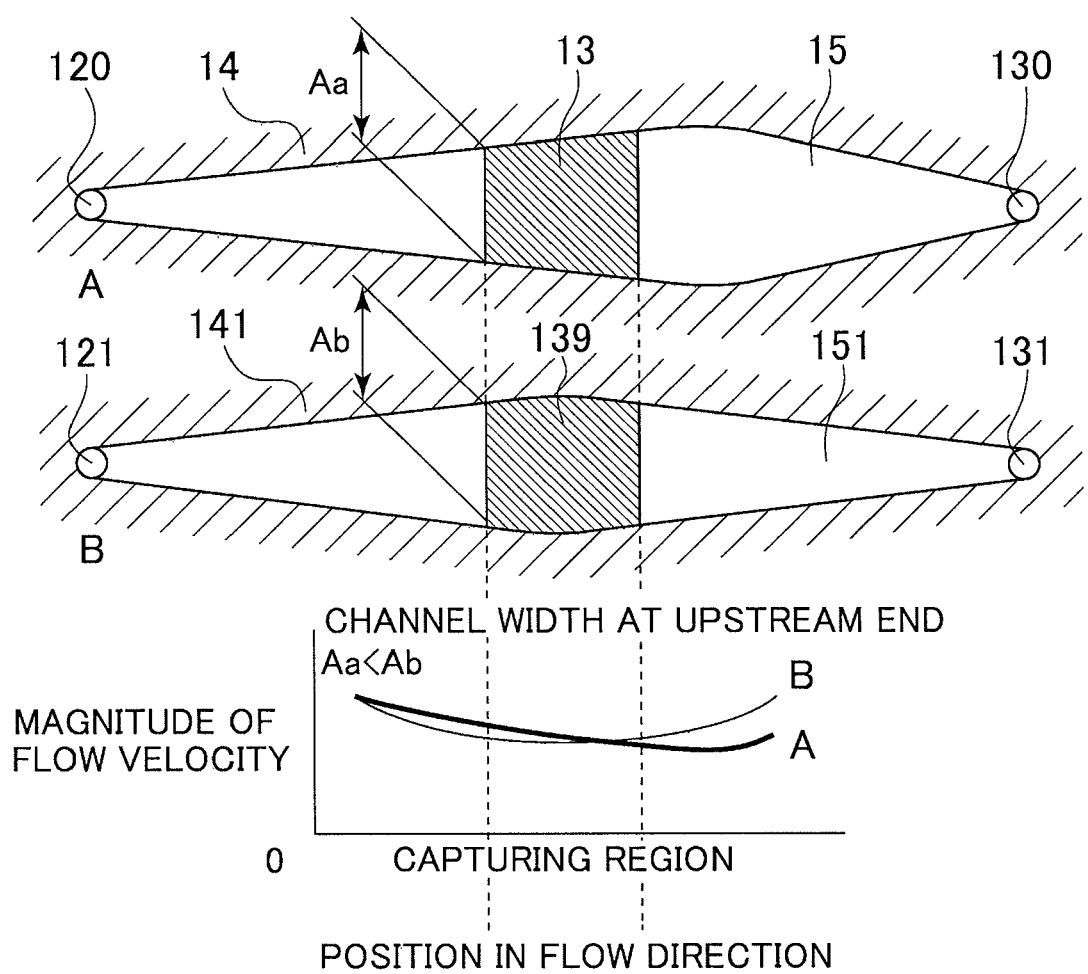
FIG. 21 is a diagram that shows the flow channel used in the embodiment, the flow channel used in the comparative example, and flow velocity distributions of respective capturing positions.

FIG. 21 is a diagram that shows the flow channel 15 in the present example shown in FIGS. 19A and 19B, the flow channel 151 in the comparative example shown in FIGS. 20A and 20B, and flow velocity distributions of the respective capturing positions 13, 139.

Diagram A of the upper flow channel in FIG. 21 shows the flow channel 15 and periphery in the present example shown in FIGS. 19A and 19B, and diagram B of the lower flow channel in FIG. 21 shows the flow channel 151 and periphery in the comparative example shown in FIGS. 20A and 20B. The graph in FIG. 21, showing the respective flow velocity distributions in diagrams A, B, represents a magnitude of average flow velocities in a perpendicular direction relative to the flow direction. The average flow velocities at the respective capturing positions in the longitudinal direction of the magnet are plotted on a horizontal axis, and the average flow velocities at the respective capturing positions in the flow direction of the fluid in the flow channel are plotted on a vertical axis. Flow channel width Aa at an upstream end of the capturing position 13 in diagram A showing the upper flow channel in FIG. 21 is smaller than flow channel width Ab at an upstream end of the capturing position 139 in diagram B showing the lower flow channel in FIG. 21. In other words, the upper flow channel, shown in diagram A of FIG. 21, is constructed to have a larger cross-sectional area at the upstream end of the capturing position 13 (magnetic particles capturing region) than a cross-sectional area that the lower flow channel, shown in diagram B of FIG. 21, has at the upstream end of the capturing position 139 (magnetic particles capturing region).

As shown in the graph of FIG. 21, it can be seen that the flow channel 151 in the comparative example shown in FIGS. 20A and 20B exhibits a constant, cross-sectional average linear flow velocity at the capturing position 139 (the magnetic particles capturing region). In contrast to this, it can be seen that the flow channel 15 in the present example shown in FIGS. 19A and 19B exhibits a monotonous decrease in cross-sectional average linear flow velocity at the capturing position 13 (the magnetic particles capturing region). One of the reasons for this is that since the fluid flowing through the flow channel 15 is a non-compressive fluid, as the cross-sectional area of the channel changes, the cross-sectional average flow velocity also needs to change so that mass (volume) is conserved.

In the flow channel 151 according to the comparative example shown in FIGS. 20A and 20B, the flow channel width at the capturing position 139 is substantially constant and the channel height is also constant, so the cross-sectional average linear flow velocity at the capturing position 139 (the magnetic particles capturing region) is constant. In the flow channel 15 according to the present example shown in FIGS. 19A and 19B, on the other hand, the flow channel width at the capturing position 13 (the magnetic particles capturing region) increases both monotonously and linearly, so the cross-sectional average linear flow velocity at the capturing position 13 (the magnetic particles capturing region) decreases monotonously.

In the flow channel 15 according to the present example shown in FIGS. 19A and 19B, increasing the flow channel area progressively at the capturing position 13 reduces the linear flow velocity inversely as that area. The fact that the cross-sectional average linear flow velocity decreases at the capturing position 13 with the downstream flow of the fluid reduces a flow velocity-dependent force that the fluid imparts to the magnetic particles. The result is that since the magnetic particles that have flown out in a non-captured condition become more susceptible to an attraction force of the magnet 12, the number of magnetic particles captured at the downstream end, in particular, will increase, which will in turn improve a capture ratio of the magnetic particles, particularly at the downstream end.

Figure 22:
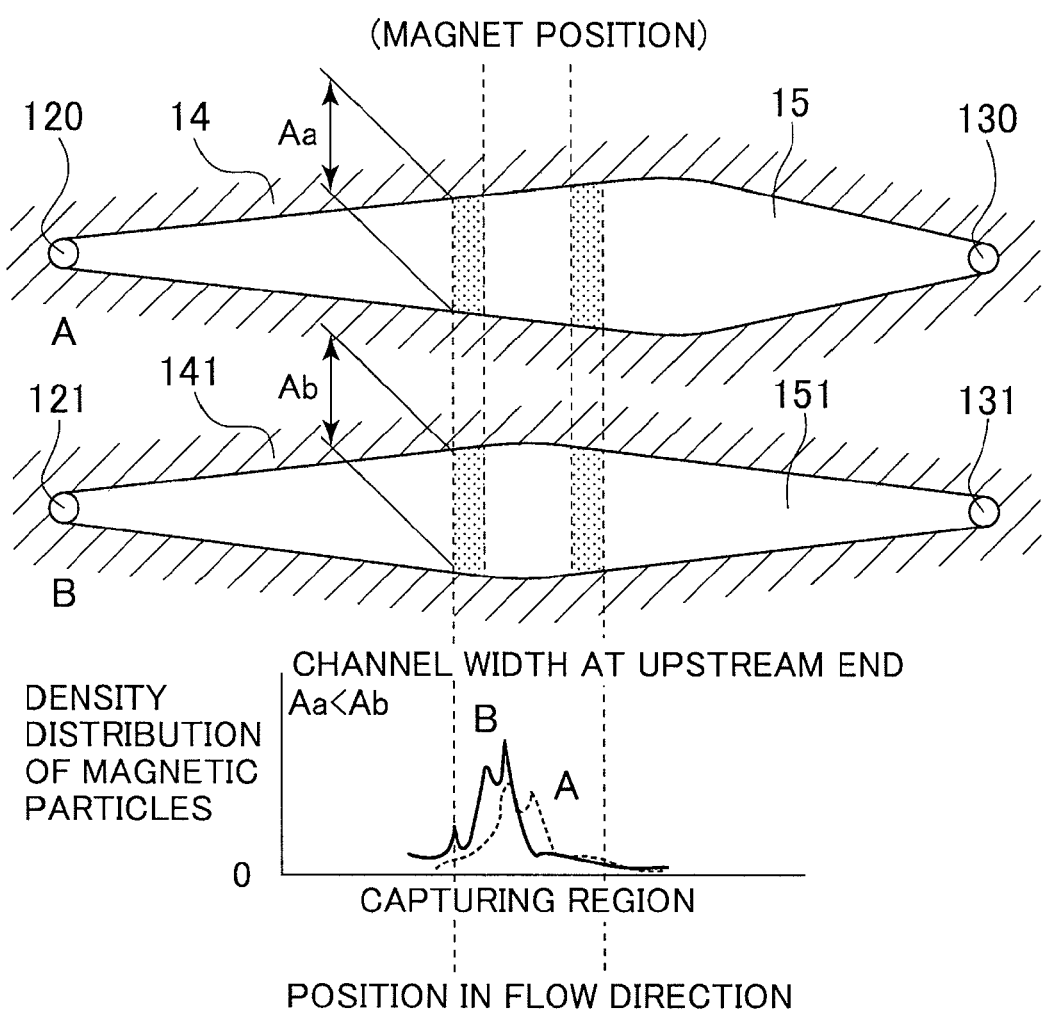
FIG. 22 is another diagram that shows the flow channel used in the embodiment, the flow channel used in the comparative example, and density distributions of the magnetic particles as captured on respective capturing positions.

FIG. 22 is another diagram that shows the flow channel 15 according to the present example shown in FIGS. 19A and 19B, the flow channel according to the comparative example shown in FIGS. 20A and 20B, and density distributions of the particles as captured on the respective capturing positions 13, 139.

Diagram A of the upper flow channel in FIG. 22 shows the flow channel 15 used in the present example of FIGS. 19A and 19B, the channel 15 being substantially the same as the upper flow channel shown in diagram A of FIG. 21. Diagram B of the lower flow channel in FIG. 22 shows the flow channel 151 used in the comparative example of FIGS. 20A and 20B, the channel 151 being substantially the same as the lower flow channel shown in diagram B of FIG. 22. The graph in FIG. 22, showing the density distributions of the particles captured in the flow channels shown as A, B, represents average density distributions of the magnetic particles in a perpendicular direction relative to the flow direction. The average density distributions at the respective capturing positions in the longitudinal direction of the magnet are plotted on a horizontal axis, and the average density distributions at the respective capturing positions in the flow direction of the fluid in the flow channel are plotted on a vertical axis.

The graph of FIG. 22 indicates that in the flow channel 151 according to the comparative example shown in FIGS. 20A and 20B, a large number of magnetic particles are captured upstream of the capturing position 139. The graph of FIG. 22 also indicates that in the flow channel 15 according to the present example shown in FIGS. 19A and 19B, a high rate of capture only at the upstream side of the capturing position 13 is improved for an even more uniform capture at the entire capturing position 13.

The behavior of particles depends on the balance of the forces applied to the particles, that is, the flow velocity-dependent force that the flow imparts to the particles, and the force applied from the magnet, that is, magnetic force. The force that the flow imparts to the particles is affected by a projection area of the particles, a velocity of the particles, and other factors. In addition, since the magnetic field gradient increases at an end of the magnet disposed near the capturing position, the force that the magnet exerts on the magnetic particles is augmented, which then causes a larger number of particles to be captured at the upstream side with high concentration of magnetic particles.

In the flow channel 151 according to the comparative example shown in FIGS. 20A and 20B, the flow channel width at the capturing position 139 is substantially constant and the channel height is also constant. A number of magnetic particles have therefore been captured upstream of the capturing position 139. At the capturing position 139 provided for capturing the magnetic particles 10, the flow channel 151 has been substantially uniform in cross-sectional shape and hence, substantially constant in linear flow velocity. This means that at the capturing position 139 provided to capture the magnetic particles, the magnetic particles 10 have experienced substantially the same force applied from the fluid. At the downstream side of the capturing position 139, therefore, the force imparted from the fluid to the magnetic particles 10 has been greater than the magnetic force attracting the magnetic particles to the capturing position. That is why the magnetic particles that had not been captured upstream of the capturing position 139 have flown out without being captured downstream thereof, either.

As opposed to this, in the flow channel 15 according to the present example shown in FIGS. 19A and 19B, the flow channel width Aa at the upstream end of the capturing position 139 is smaller than the width Ab of the flow channel 151, at the upstream end of the capturing position 13, in the comparative example of FIGS. 20A and 20B. The flow channel cross-sectional area is therefore small and thus the cross-sectional average linear flow velocity is high, such that the high capture ratio at the upstream side of the capturing position 139 is improved, that is, reduced. Additionally, since the flow channel width at the capturing position 13 (the magnetic particles capturing region) increases both monotonously and linearly, the cross-sectional average linear flow velocity at the capturing position 13 decreases as the fluid goes downstream thereof. This decrease diminishes the flow velocity-dependent force that the fluid imparts to the magnetic particles. The result is that since the magnetic particles that have flown out in a non-captured condition become more susceptible to the attraction force of the magnet 12, the number of magnetic particles captured at the downstream end will increase, which will in turn improve the capture ratio of the magnetic particles, particularly at the downstream end, and suppress the nonuniformity of capture at the entire capturing position 13. Briefly, the uniform capture of magnetic particles at the entire capturing position 13 is expected to improve B/F separation and cleaning efficiency, enhance measurement accuracy, and raise reproducibility of measurement results.

Figure 23:
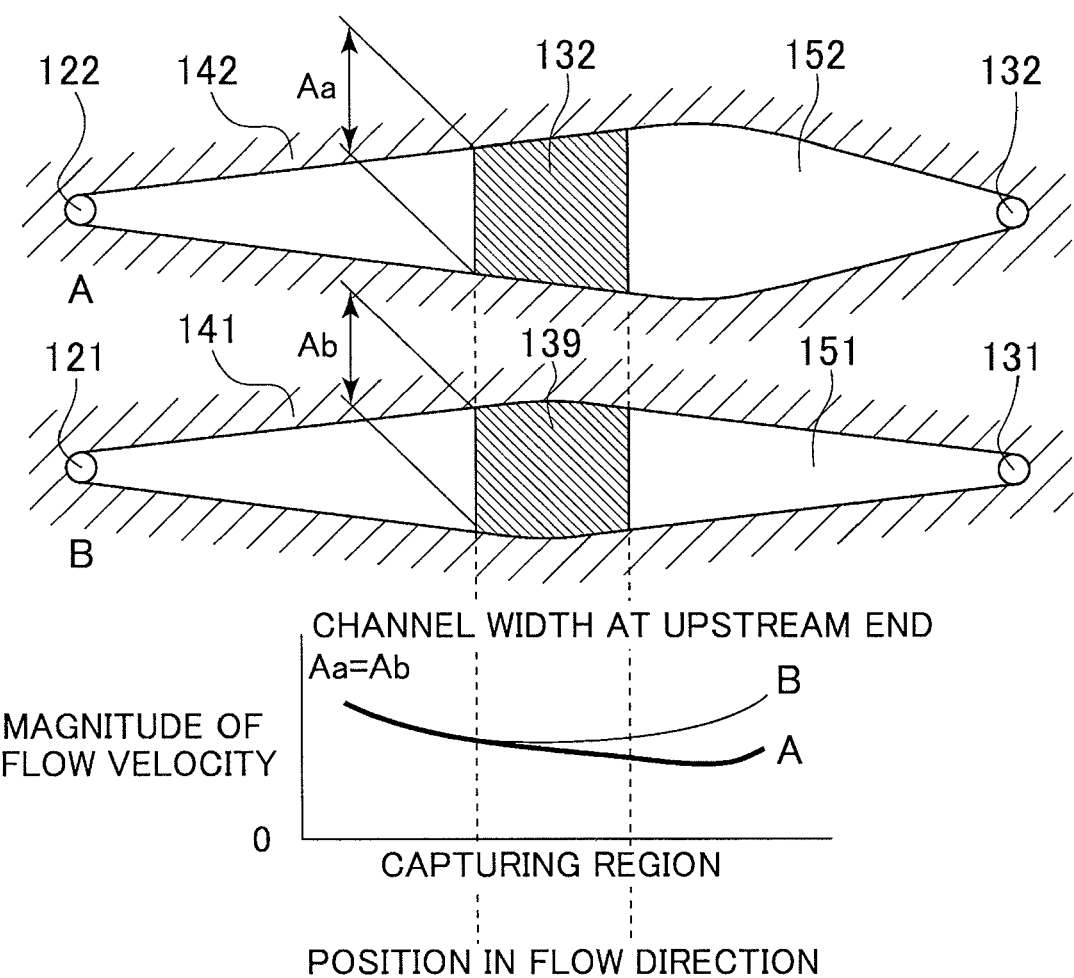
FIG. 23 is a diagram that shows a flow channel used in a modification of the embodiment, the flow channel used in the comparative example, and a flow velocity distribution of respective capturing positions.

FIG. 23 is a diagram that shows a flow channel 152 used as a modification of the channel 15 in the present example of FIGS. 19A and 19B, the flow channel 151 used in the comparative example of FIGS. 20A and 20B, and flow velocity distributions of respective capturing positions 132, 139.

The upper flow channel, marked with symbol A in FIG. 23, differs from the upper flow channel in FIG. 21 in that the upper flow channel A in FIG. 23 is formed so that width Aa of the flow channel, at an upstream end of the capturing position 132, is the same as the width Ab of the lower flow channel 151, marked with symbol B in FIG. 23, at the upstream end of the capturing position 139.

As shown in the graph of FIG. 23, cross-sectional average linear flow velocity decreases particularly at the capturing position 132 (the magnetic particles capturing region) as the fluid goes downstream thereof. Unlike the graph of FIG. 21, however, the graph of FIG. 23 indicates that the cross-sectional average linear flow velocity decreases in a similar pattern between the upstream end of the capturing position 139 of the flow channel 151 in the comparative example of FIGS. 20A and 20B, and the upstream end of the capturing position 132 of the flow channel 152 in the present example of FIGS. 19A and 19B. For this reason, compared with the flow channel 15 of the present example that is shown in FIGS. 19A and 19B for structural understanding and in FIG. 21 for comparison purposes, the flow channel 132 in FIG. 23 is estimated to cause a number of magnetic particles to be captured upstream of the capturing position 132. To correct this capture state, the flow channel is preferably constructed so that the flow channel width at the upstream end of the capturing position 132 is suitably reduced for lower cross-sectional average linear flow velocity at the upstream end of the capturing position 132 (the magnetic particles capturing region). Additionally, in order that the cross-sectional average linear flow velocity at the downstream end of the capturing position 132 (the magnetic particles capturing region) becomes even lower than the cross-sectional average linear flow velocity at the upstream end of the capturing position 132, the flow channel width at the upstream end of the capturing position 132 is reduced below the flow channel width at the downstream end of the capturing position 132. The flow channel is preferably constructed to increase at least the channel cross-sectional area at the upstream end of the capturing position 132.

It has been described in the above example that the cross-sectional average linear flow velocity at the magnetic particles capturing region in the flow channel is reduced monotonously by increasing the flow channel width at the capturing region both monotonously and linearly between the upstream side and the downstream side, with respect to the flow direction of the fluid (the sample). Instead, however, the cross-sectional average linear flow velocity is suitably reduced monotonously by maintaining constant flow channel width and increasing only the flow channel height at the magnetic particles capturing region both monotonously and linearly. Another suitable alternative is to reduce the cross-sectional average linear flow velocity by increasing both of the flow channel height and flow channel width of the magnetic particles capturing region monotonously between the upstream side and the downstream side, with respect to the flow direction of the fluid (the sample). Changing the flow channel height, however, involves changing one or both of upper and lower walls of the flow channel in thickness and is therefore likely to cause optical problems, for which reason, adjusting the flow channel width is most preferred.

It has also been described in the above example that the flow channel is constructed so that its width from the channel inlet to a further downstream position relative to the downstream end of the capturing position increases both monotonously and linearly between the upstream side and the downstream side, with respect to the flow direction of the fluid (the sample). In addition to this, the flow channel is constructed so that its width from the further downstream position relative to the downstream end of the capturing position, to the channel outlet, decreases both monotonously and linearly between the upstream side and the downstream side, with respect to the flow direction of the fluid (the sample). Suitably, however, the flow channel may not be constructed so that its width from the channel inlet to the further upstream position relative to the upstream end of the capturing position increases both monotonously and linearly between the upstream side and the downstream side, with respect to the flow direction of the fluid (the sample). This may instead be achieved by, for example, keeping the width of the flow channel constant and/or keeping its cross-sectional area constant. In addition, the flow channel may suitably not be constructed so that its width from the further downstream position relative to the downstream end of the capturing position, to the channel outlet, decreases both monotonously and linearly between the upstream side and the downstream side, with respect to the flow direction of the fluid (the sample). This may instead be achieved by, for example, keeping the width of the flow channel constant and/or keeping its cross-sectional area constant. In consideration of more stable supply of the liquid and more efficient cleaning and B/F separation, however, a flow channel shape that increases or reduces the width and/or cross-sectional area of the flow channel both monotonously and linearly is most appropriate since diffusers generally have a separation angle of 8 degrees or so.

Furthermore, the configuration where the flow channel width at the capturing position increases both monotonously and linearly between the upstream side and the downstream, with respect to the flow direction of the fluid (the sample) has been described in the above example. The increase, however, does not always need to be monotonous and linear. It suffices if at least the flow channel width at the capturing position increases monotonously between the upstream side and the downstream, with respect to the flow direction of the fluid (the sample). It also suffices if the flow channel width at the downstream end of the capturing position is greater than the flow channel width at the upstream end of the capturing position. In addition, it suffices if the flow channel cross-sectional area at the downstream end of the capturing position (the magnetic particles capturing region) is greater than the flow channel cross-sectional area at the upstream end of the capturing position (the magnetic particles capturing region). That is to say, the region between the upstream end and downstream end of the capturing position may have a shape that can be expressed by a general function, for example a function approximated by a polynomial, exponential function, or trigonometric function. In consideration of more stable supply of the liquid and more efficient cleaning and B/F separation, however, a flow channel shape that increases or reduces the width and/or cross-sectional area of the flow channel both monotonously and linearly is most appropriate since diffusers generally have the separation angle of 8 degrees or so.

Fourth Example

Further Example of the Invention

While an embodiment of the present invention has been described in detail above, the invention is not limited to or by the embodiment and may be changed or modified in various forms without departing from the scope of the invention. For instance, one form may apply both of the description given in the first example and that of the third example or may apply both of the description given in the second example and that of the third example.

Preferred Modes of the Invention

The following summarizes preferred modes of the present invention.

Provided according to a first further mode of the present invention is a sample analyzing device comprising a flow channel, a sample liquid that contains magnetic particles and flows through the flow channel, and magnetic field generating means for generating magnetic fields to capture the magnetic particles in the flow channel. The magnetic fields generated by the magnetic field generating means have a magnitude that increases in a direction heading from an upstream side of the flow channel, towards a downstream side thereof.

In the sample analyzing device of the first further mode, the magnetic field generating means is preferably a magnet, the magnet being disposed in an inclined condition with respect to a direction in which the sample liquid moves from the upstream side of the flow channel, towards the downstream side thereof.

In the sample analyzing device of the first further mode, the magnetic field generating means preferably includes a plurality of magnets, the magnets each being disposed to be closer to the flow channel as the channel heads from the upstream side thereof, towards the downstream side.

In the sample analyzing device of the first further mode, the magnetic field generating means preferably includes a plurality of electromagnets, the electromagnets each increasing in a number of windings of a coil as the coil goes in a direction heading from the upstream side of the flow channel, towards the downstream side thereof.

Provided according to a second further mode of the present invention is a magnetic particles capturing method, employing magnetic field generating means to capture magnetic particles contained in a sample liquid flowing through a flow channel. Magnetic fields generated by the magnetic field generating means have a magnitude that increases in a direction heading from an upstream side of the flow channel, towards a downstream side thereof.

Provided according to a third further mode of the present invention is a sample analyzing device comprising a flow channel for conducting a sample liquid containing magnetic particles into the flow channel, a magnet provided outside the flow channel, the magnet generating, in the flow channel, magnetic fields to capture the magnetic particles on a particles capturing region of the flow channel, and means for analyzing the captured magnetic particles. A distance between the flow channel and the magnet is longer at an upstream side of the magnet than at a downstream side thereof, such that the magnetic fields that the magnet generates in the flow channel have a greater magnitude at a downstream side of the flow channel than at a upstream side thereof.

In the sample analyzing device of the third further mode, the magnet preferably has a shape obtained by removing the upstream side of the magnet that is opposed to the flow channel, from a regular parallelepiped or columnar body.

In the sample analyzing device of the third further mode, the regular parallelepiped or columnar body preferably has a longitudinal face pointing in a direction substantially orthogonal to a particles capturing surface of the flow channel.

The columnar body or regular parallelepiped in the sample analyzing device of the third further mode preferably includes a face opposed to the flow channel, the face being substantially parallel to a particles capturing surface of the channel.

In the sample analyzing device of the third further mode, the magnetic fields of the magnet are preferably oriented in a direction substantially parallel or substantially perpendicular to a particles capturing surface of the flow channel.

In the sample analyzing device of the third further mode, an angle that a face of the magnet that is opposed to the flow channel forms with the channel is preferably greater at the upstream side than at the downstream side.

In the sample analyzing device of the third further mode, an angle that an upstream side of an upper surface of the magnet preferably forms with the magnetic particles capturing surface is 15 to 45 degrees.

In the sample analyzing device of the third further mode, preferably a face of the magnet that is opposed to the flow channel, and the magnetic particles capturing region are substantially parallel at the downstream side.

In the sample analyzing device of the third further mode, at the upstream side, the magnitude of the magnetic fields generated in the flow channel, preferably increases progressively as the channel goes downstream, and at the downstream side, the magnitude of the magnetic fields is greater than at the upstream side, a position-dependent change in the magnitude of the magnetic fields being less significant than at the upstream side.

In the sample analyzing device of the third further mode, the magnet is preferably a single permanent magnet or electromagnet.

Provided according to a fourth further mode of the present invention is a sample analyzing device comprising a flow channel for conducting a sample liquid containing magnetic particles into the flow channel, and magnetic field generating means for generating magnetic fields to capture the magnetic particles in a magnetic particles capturing region of the flow channel. The flow channel is constructed to have a larger channel cross-sectional area at a downstream end of the magnetic particles capturing region than a channel cross-sectional area at an upstream end of the magnetic particles capturing region.

In the sample analyzing device of the fourth further mode, the flow channel is preferably constructed so that the channel cross-sectional area at the magnetic particles capturing region increases monotonously between an upstream side and a downstream side.

In the sample analyzing device of the fourth further mode, the magnetic particles capturing region of the flow channel is preferably constructed to reduce a linear flow velocity of the magnetic particles monotonously between an upstream side and a downstream side.

In the sample analyzing device of the fourth further mode, the flow channel is preferably constructed so that width of the channel, at the magnetic particles capturing region, increases monotonously between an upstream side and a downstream side.

In the sample analyzing device of the fourth further mode, the flow channel is preferably constructed so that height of the channel, at the magnetic particles capturing region, increases monotonously between an upstream side and a downstream side.

Provided according to a fifth further mode of the present invention is a sample analyzing method comprising: conducting a sample containing magnetic particles into a flow channel, generating magnetic fields in a magnetic particles capturing region of the flow channel by magnetic field generating means, and capturing the magnetic particles. The sample is supplied to the magnetic particles capturing region constructed for the flow channel to have a larger cross-sectional area at a downstream end than a cross-sectional area at an upstream end. The magnetic fields are generated by the magnetic field generating means, and the magnetic particles are captured.

DESCRIPTION OF REFERENCE NUMBERS

10 Magnetic particle
11 Magnet
12 Magnet or electromagnet
13 capturing position
14 Flow channel wall
15 Flow channel
16 Sliding mechanism
17 Condensing lens
18 Laser light source
21, 22, 23 Tubes
24 Sipper nozzle
25 Pump
26 Arm
30, 31 Valves
32 Suspension container
33 Detergent container
34 Waste liquid container
35 Cleaning mechanism
36 Reaction unit
37 Controller
38 Signal line
39 Photodetector
41, 42, 43, 44 Magnets

The invention claimed is:

1. A sample analyzing device comprising:
a flow channel, defined by flow channel walls, that conducts a sample including magnetic particles in a flow direction, at least a portion of the flow channel walls being formed from a transparent material;
a magnet that generates magnetic fields for capturing the magnetic particles in a magnetic particles capturing region located within a transparent flow channel wall section adjacent to the magnet, the magnetic particles capturing region including an upstream side, a downstream side, a length parallel to the flow direction, and a width, perpendicular to the flow direction, that increases linearly from the upstream side to the downstream side, the magnet being disposed in an inclined condition with respect to the flow direction from the upstream side of the magnetic particles capturing region towards the downstream side, and the magnetic fields having a greater magnitude at the downstream side of the magnetic particles capturing region than at the upstream side; and
a detector that detects light transmitted through the magnetic particles capturing region.

2. A sample analyzing device comprising:
a flow channel, defined by flow channel walls, that conducts a sample including magnetic particles in a flow direction, at least a portion of the flow channel walls being formed from a transparent material;
a plurality of magnets that generate magnetic fields for capturing the magnetic particles in a magnetic particles capturing region located within a transparent flow channel wall section adjacent to the magnets, the magnetic particles capturing region including an upstream side, a downstream side, a length parallel to the flow direction, and a width, perpendicular to the flow direction, that increases linearly from the upstream side to the downstream side, the magnets each being disposed to be closer to the magnetic particles capturing region in a direction heading from the upstream side towards the downstream side, and the magnetic fields having a greater magnitude at the downstream side of the magnetic particles capturing region than at the upstream side; and
a detector that detects light transmitted through the magnetic particles capturing region.

3. A sample analyzing device comprising:
a flow channel, defined by flow channel walls, that conducts a sample including magnetic particles in a flow direction, at least a portion of the flow channel walls being formed from a transparent material;
a plurality of electromagnets that generate magnetic fields for capturing the magnetic particles in a magnetic particles capturing region located within a transparent flow channel wall section adjacent to the electromagnets, the magnetic particles capturing region including an upstream side, a downstream side, a length parallel to the flow direction, and a width, perpendicular to the flow direction, that increases linearly from the upstream side to the downstream side, the electromagnets each increasing in a number of windings of a coil in a direction heading from the upstream side of the magnetic particles capturing region towards the downstream side thereof, and the magnetic fields having a greater magnitude at the downstream side of the magnetic particles capturing region than at the upstream side; and
a detector that detects light transmitted through the magnetic particles capturing region.

4. The sample analyzing device according to claim 1, wherein:
the flow channel is constructed so that the channel cross-sectional area at the magnetic particles capturing region increases monotonously between the upstream side and the downstream side.

5. The sample analyzing device according to claim 1, wherein:
the magnetic particles capturing region reduces a linear flow velocity of the magnetic particles monotonously between the upstream side and the downstream side.

6. The sample analyzing device according to claim 4, wherein:
the flow channel is constructed so that a width of the channel, at the magnetic particles capturing region, increases monotonously from the upstream side to the downstream side.

7. The sample analyzing device according to claim 4, wherein:
the flow channel is constructed so that a height of the channel, at the magnetic particles capturing region, increases monotonously between an upstream side and a downstream side.

8. The sample analyzing device according to claim 1, wherein: the magnet has a length in the flow direction that is smaller than the length of the magnetic particles capturing region.

9. The sample analyzing device according to claim 8, wherein: the magnet has an upstream side positioned downstream of the upstream side of the magnetic particles capturing region, and, at the same time, a downstream side positioned upstream of the downstream side of the magnetic particles capturing region.

10. The sample analyzing device according to claim 2, wherein:
the flow channel is constructed so that the channel cross-sectional area at the magnetic particles capturing region increases monotonously between the upstream side and the downstream side.

11. The sample analyzing device according to claim 2, wherein:
the magnetic particles capturing region reduces a linear flow velocity of the magnetic particles monotonously between the upstream side and the downstream side.

12. The sample analyzing device according to claim 10, wherein:
the flow channel is constructed so that a width of the channel, at the magnetic particles capturing region, increases monotonously from the upstream side to the downstream side.

13. The sample analyzing device according to claim 10, wherein:
the flow channel is constructed so that a height of the channel, at the magnetic particles capturing region, increases monotonously between an upstream side and a downstream side.

14. The sample analyzing device according to claim 2, wherein: the magnets have a length in the flow direction that is smaller than the length of the magnetic particles capturing region.

15. The sample analyzing device according to claim 14, wherein: the magnets have an upstream side positioned downstream of the upstream side of the magnetic particles capturing region, and, at the same time, a downstream side positioned upstream of the downstream side of the magnetic particles capturing region.

16. The sample analyzing device according to claim 3, wherein:
the flow channel is constructed so that the channel cross-sectional area at the magnetic particles capturing region increases monotonously between the upstream side and the downstream side.

17. The sample analyzing device according to claim 3, wherein:
the magnetic particles capturing region reduces a linear flow velocity of the magnetic particles monotonously between the upstream side and the downstream side.

18. The sample analyzing device according to claim 16, wherein:
the flow channel is constructed so that a width of the channel, at the magnetic particles capturing region, increases monotonously from the upstream side to the downstream side.

19. The sample analyzing device according to claim 16, wherein:
the flow channel is constructed so that a height of the channel, at the magnetic particles capturing region, increases monotonously between an upstream side and a downstream side.

20. The sample analyzing device according to claim 3, wherein: the electromagnets have a length in the flow direction that is smaller than the length of the magnetic particles capturing region, and said electromagnets have an upstream side positioned downstream of the upstream side of the magnetic particles capturing region, and, at the same time, a downstream side positioned upstream of the downstream side of the magnetic particles capturing region.

* * * * *